United States Patent
Hargrove et al.

(10) Patent No.: US 12,406,766 B2
(45) Date of Patent: Sep. 2, 2025

(54) METHODS AND APPARATUSES FOR MANAGING HEALTHCARE ASSETS AND PROCESSES

(71) Applicant: IntraLogic Health Solutions, Inc., Brentwood, TN (US)

(72) Inventors: Jeffrey B. Hargrove, Bancroft, MI (US); Geoffrey A. Wilson, Canton, MI (US); Jack Weiner, Bloomfield Hills, MI (US)

(73) Assignee: INTRALOGIC HEALTH SOLUTIONS, INC., Brentwood, TN (US)

( * ) Notice: Subject to any disclaimer, the term of this patent is extended or adjusted under 35 U.S.C. 154(b) by 0 days.

(21) Appl. No.: 18/650,211

(22) Filed: Apr. 30, 2024

(65) Prior Publication Data
US 2024/0290479 A1    Aug. 29, 2024

Related U.S. Application Data

(63) Continuation of application No. 17/196,930, filed on Mar. 9, 2021, now Pat. No. 12,009,092.

(60) Provisional application No. 62/986,949, filed on Mar. 9, 2020.

(51) Int. Cl.
| | |
|---|---|
| G16H 40/20 | (2018.01) |
| G06K 19/07 | (2006.01) |
| G16H 40/40 | (2018.01) |

(52) U.S. Cl.
CPC ......... *G16H 40/20* (2018.01); *G06K 19/0723* (2013.01); *G16H 40/40* (2018.01)

(58) Field of Classification Search
CPC ..... G16H 40/20; G16H 40/40; G06K 19/0723
USPC .......................................................... 705/2
See application file for complete search history.

(56) References Cited

U.S. PATENT DOCUMENTS

| | | | |
|---|---|---|---|
| 8,925,812 B2 * | 1/2015 | Schmucker | G16H 15/00 235/487 |
| 9,507,981 B2 * | 11/2016 | Dor | G06Q 10/0833 |

* cited by examiner

*Primary Examiner* — Garcia Ade
(74) *Attorney, Agent, or Firm* — Reising Ethington P.C.

(57) ABSTRACT

Healthcare asset units are enabled to accomplish a healthcare facility management objective by first preparing the asset units in a pre-processing phase by using a computational processor to determine a first unique identifier for each asset unit. The prepared asset units are then transported in a removal phase to a manufacturer location, retrofit in a manufacturing phase at the manufacturer location by applying manufacturing processes to implement the durable information identifier on each asset unit, and by using a computational processor to determine a second unique identifier for each asset unit. The prepared asset units are then transported in a return phase, from the manufacturer location to a healthcare facility where the retrofitted asset units are subsequently used to accomplish a healthcare facility management objective.

12 Claims, 19 Drawing Sheets

---

Pre-Processing Phase
- Determine and implement a first unique identifier associated with an asset unit at a facility
- Append the first unique identifier of the asset unit to a database for recording asset unit processes
- Utilize such database to include records of the life cycle and utilization of facility assets, records of the manufacture, distribution or sale of the asset unit, or records of manufacturing processes applied to the asset unit to enable a management objective

➡

Removal Phase
- Append data of a first unique identifier of an asset unit selected for removal to a database
- Temporarily affix to the asset unit a means to enable the reading of its first unique identifier
- Package the asset unit such that its first unique identifier may be utilized in a Manufacturing Phase
- Controllably transport the asset unit from a facility to a manufacturer
- Track the asset unit's movement and utilization

⬇

Manufacturing Phase
- Receive the asset unit at the manufacturer
- Append the asset unit's first unique identifier to a database used in a manufacturing process
- Carry out at least one manufacturing process on the asset unit for the purpose of retrofitting a durable information identifier on the asset unit
- Controllably transport the asset unit back to a facility
- Track the asset unit's movement and utilization

⬅

Return Phase
- Receive at a facility the asset unit transported after the Manufacturing Phase
- Detect or measure a the durable information identifier on the asset unit by using a durable information identifier detector
- Append information of the durable information identifier to a database for asset unit processes
- Physically return the asset unit to inventory at a facility for use in a management objective

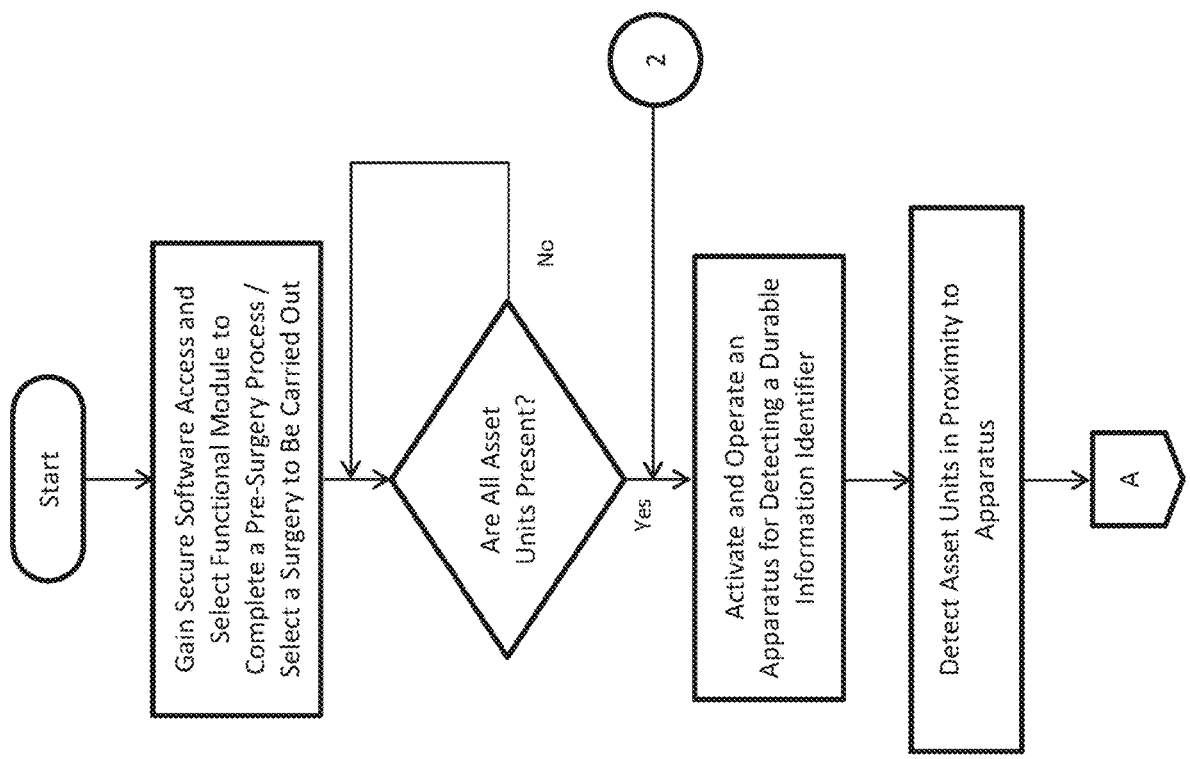

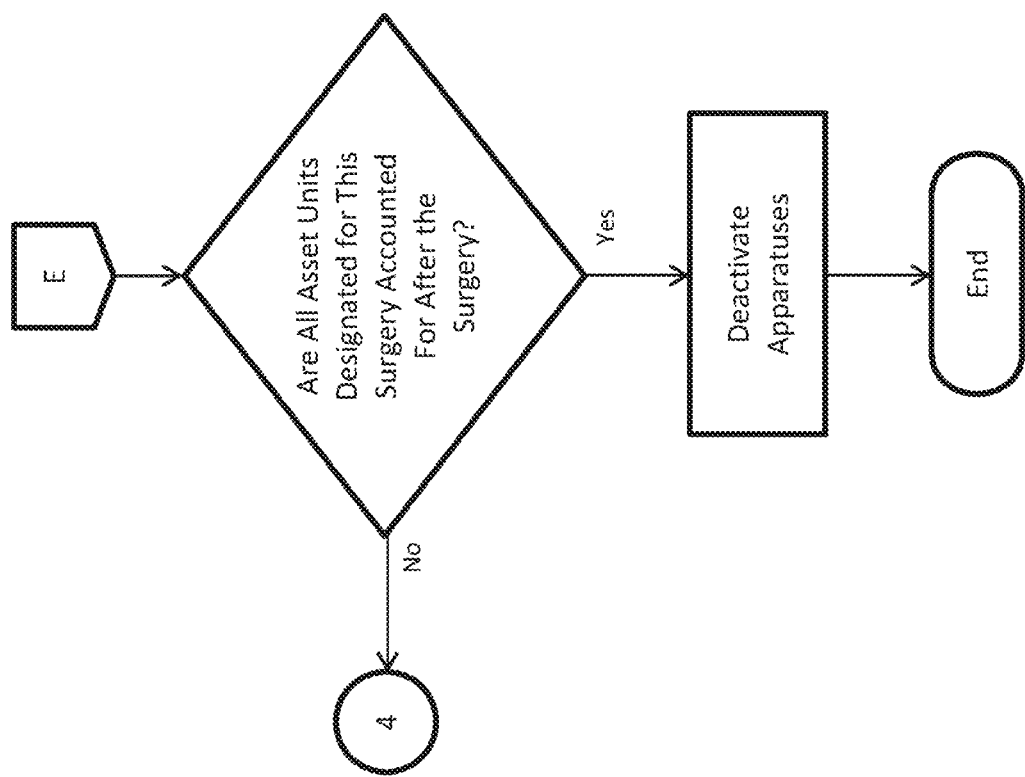

METHODS AND APPARATUSES FOR MANAGING HEALTHCARE ASSETS AND PROCESSES

CROSS-REFERENCES TO RELATED APPLICATIONS

This application is a continuation of U.S. Non-Provisional application Ser. No. 17/196,930 filed Mar. 9, 2021, which claims the benefit of U.S. Provisional Application No. 62/986,949 filed Mar. 9, 2020; which are incorporated by reference herein in their entirety.

STATEMENT REGARDING FEDERALLY SPONSORED RESEARCH OR DEVELOPMENT

Not Applicable

FIELD

This application relates generally to healthcare facility management.

BACKGROUND

Providers of healthcare, such as hospitals, ambulatory surgical centers or any other type of medical professional facility, function in an environment that requires exceptionally-focused management and control of numerous processes and assets. For recipients of services, such focus is needed to assure safety, wellbeing, appropriateness of care, quality of care, satisfaction of care and correct application of services. For healthcare providers, such focus is needed to assure quality of services, manage risks, control costs, comply with regulations and optimize relationships with associated service providers such as asset vendors. These are just a few examples of numerous aspects and justifiers of management and control, the totality of which creates a remarkably complex and demanding environment on those tasked with managerial and operational responsibility.

Despite all efforts to assure the best levels of asset and process management, problems and deficiencies persist. For example, healthcare-acquired infections cause thousands of deaths each year in the United States. Many of these can be avoided by strict adherence to preventive practices, and such practices are driven by process management. As another example, retained surgical items are surgery-related assets such as surgical instruments and other materials that are unintentionally left inside a patient after a surgical procedure. It is generally held that these errors occur due to a lack of organization and communication between surgical staff during the process. While not statistically common, the danger to patient safety and subsequent costs associated with remediation are considerable. These two examples are mere illustrations of numerous other problems that arise from deficiencies in asset and process management.

Efforts to address these deficiencies are equally numerous and all attempt to create remedies at multiple levels. Many of these also serve to comply with regulations and laws aimed at assuring safety and quality of services. Non-technical policies and procedures are articulated for purposes of process and asset management. Just one of many examples is the use of manual counting of surgical assets before and after a surgery, with the intent being to eliminate retained surgical items. Simply put, one or more provider personnel, such as nurses and medical technicians, make a manual count of assets present before a surgery, and then they repeat the count after the surgery. Such process, while well-intended, is highly limited by the fact that human errors still occur. It is also a time-consuming and therefore costly process.

There are many technological approaches to management of healthcare facility assets and processes taught in the art, many of which seek to remedy deficiencies or improve existing processes. For example, uses of barcoding and radio frequency identification (RFID) technologies have been conceived and reduced to practice for hospital asset management. Other example technological approaches include utilization of various optical recognition techniques, the use of arrays of dots, and transmitter, sensor or transducer devices such as Bluetooth devices and magnetic devices.

While offering significant advantages and opportunities for management improvement, a number of limitations to actual implementation and reduction to practice persist in many areas of potential use in the healthcare setting. For example, RFID tracking of existing surgical instrument inventories is technically feasible. However, a process is needed that enables surgical instruments to be retrofitted with RFID chips (i.e. RFID tags) such that: (1) the RFID chips are placed on instruments in a way that minimizes chances that the RFID chip may dislodge from the instrument, (2) the RFID chips will not retain biomaterials that may foster infectious agents, (3) the instrument can still meet sterilization standards through common means such as autoclaving, (4) the RFID chips are covered with biocompatible materials, (5) the RFID chip placement location optimizes the ability for the chip to be detected by RFID reading (i.e. scanning) instrumentation, and (6) such processes are done in a way that permits very large inventories of surgical instruments to be retrofitted in a way that does not disrupt the healthcare facility's normal functions. This last aspect is highly important. Put simply, healthcare facilities cannot shut down surgical functions for weeks or months while its surgical instruments are being retrofitted with RFID chips. Further to that, such retrofitting processes need to be aligned with applicable regulations such as the FDA's Quality Systems Regulation (21 CFR 820) and with the healthcare facility's need for documented chain of custody of its assets. Further still, methods and apparatuses are needed that improve or enable the acquisition of data associated with healthcare facility assets and processes, that accurately condition and process such data, and that utilize such data through practical applications of software. Just one non-limiting example of such data is data arising from the use of RFID technologies for tracking healthcare facility assets or for measuring characteristics of healthcare facility processes.

SUMMARY

A method is provided for enabling asset units to accomplish a healthcare facility management objective, wherein each asset unit carries a durable information identifier. The method comprises the steps of preparing asset units in a pre-processing phase by using a computational processor to determine a first unique identifier for each asset unit, transporting the prepared asset units in a removal phase, to a manufacturer location, retrofitting the prepared asset units in a manufacturing phase at the manufacturer location by applying manufacturing processes to implement the durable information identifier on each asset unit, and by using a computational processor to determine a second unique identifier for each asset unit, and transporting the prepared asset units in a return phase, from the manufacturer location to a healthcare facility where the retrofitted asset units are subsequently used for a healthcare facility management objective.

A healthcare facility process management method is provided wherein data from an asset management system provides information used to manage a healthcare facility process. The method comprises the steps of operating an asset management system comprising a plurality of asset units, each asset unit carrying a durable information identifier, utilizing durable information identifier detectors to obtain data for quantifying or qualifying asset unit use at points of healthcare facility processes performed on the asset units, processing the data relating to asset unit use at points of healthcare facility processes to obtain additional data related to the carrying out of such facility processes, identifying healthcare facility processes to be measured or analyzed, retrieving process data from an asset management system by using a computational means, and analyzing the data by using a computational means, wherein the analyzed data provide measures and characteristics of the managed healthcare facility processes.

A method is provided for managing assets and healthcare facility processes by tracking uses of asset units in a healthcare facility. The method comprises the steps of retrofitting asset units with a durable information identifier, initiating facility operational process use of the asset units, wherein durable information identifier detectors configured to detect or measure the durable information identifier of the asset units are utilized, and wherein information received by the durable information identifier detectors is appended to databases containing information about the asset units as utilized by a facility for asset and process management, tracking process uses of the asset units in a facility, wherein durable information identifier detectors configured to detect a durable information identifier of the asset units are utilized in relation to the facility operational processes, and wherein information received by the durable information identifier detectors is appended to databases containing information about the asset units as utilized by a facility for asset and process management, acquiring additional data related to at least one healthcare facility operational process, wherein devices configured to acquire such additional data are utilized in relation to the facility operational processes, and wherein information received by the devices is appended to databases containing information about each process use, and operationally coupling the devices and durable information identifier detectors to a data acquisition system, wherein coupling is achieved by interfacing the devices and durable information identifier detectors to an information technology platform utilizing a computer-based data acquisition system linked to databases, wherein the devices and durable information identifier detectors further comprise computer-based systems including computers, processors, memory, displays or peripheral devices, and wherein computer-based systems utilize software practically applied to control the devices and durable information identifier detectors.

DRAWING DESCRIPTIONS

These and other features and advantages will become apparent to those skilled in the art in connection with the following detailed description and drawings of one or more embodiments of the invention, in which:

FIG. 1 shows a block diagram of method steps for coordinating the removal of assets from a facility to enable the assets for a management objective;

FIG. 2 a block diagram of method steps for an integrated facility asset and process management system;

FIGS. 11a-11f show flowcharts of software practically applied to complete processes in an operating room.

DETAILED DESCRIPTION

Disclosed herein are a number of methods and apparatuses for improving healthcare asset and process management, and for enabling practical implementation of the methods and apparatuses in a healthcare facility setting. Many of the methods disclosed may be reduced to practice through the operation of a system of the inventive aspects taught herein.

As utilized throughout, the term "asset" or "assets" is meant to refer to any one or more objects either possessed by or utilized by a healthcare facility. The term "asset type" is meant to refer to any particular form or classification of an asset. The term "asset unit" is meant to refer to a single instance of an asset or an asset type. A non-limiting example of just one distinction of use for these terms is to consider "assets" as the totality of all surgical instruments utilized in a healthcare facility; to consider "asset type" to refer to all surgical clamps as a subset of the assets; and to consider an "asset unit" as referring to any single instance of a surgical clamp.

Figure 1:
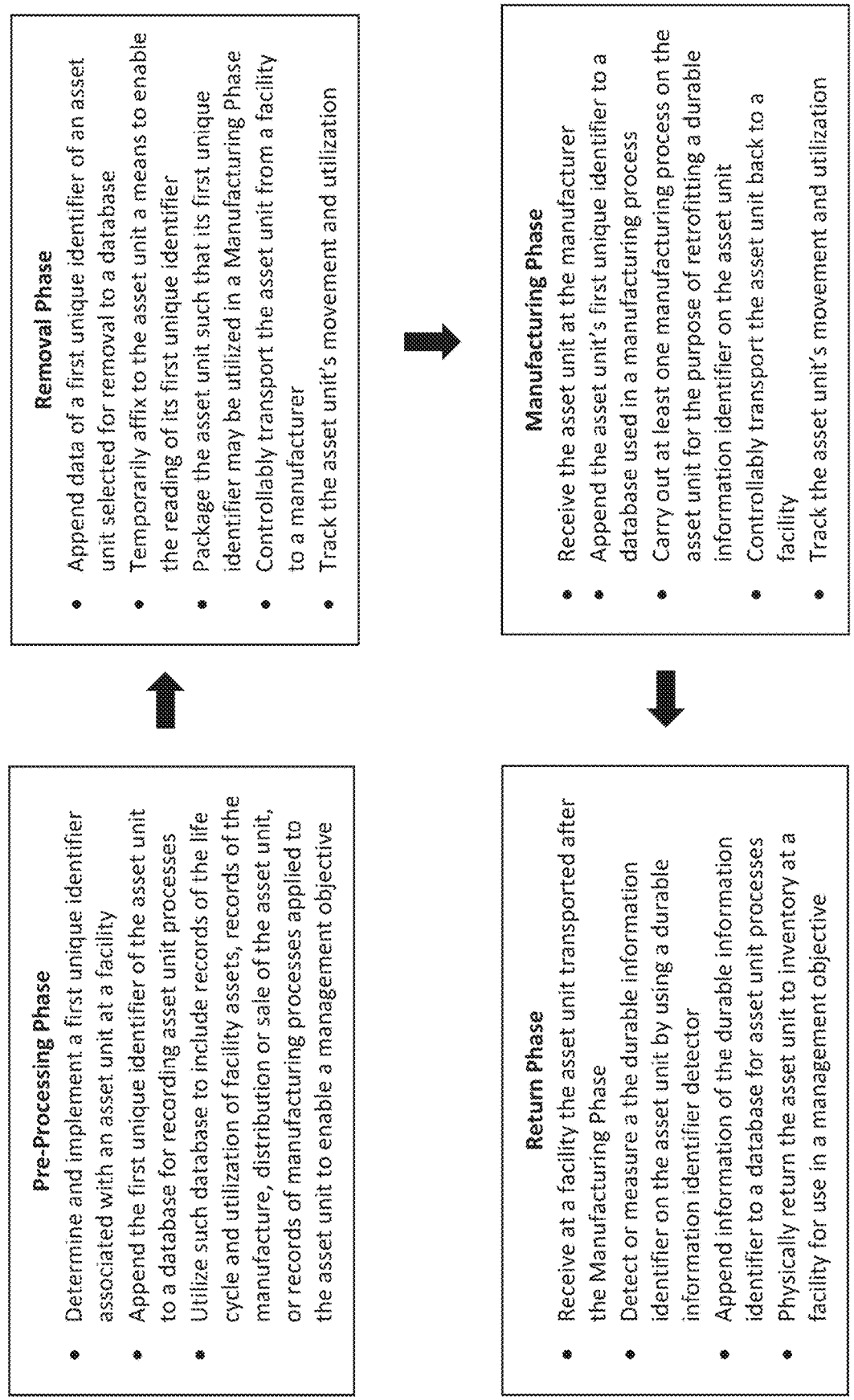

FIG. 1 shows a block diagram of method steps for coordinating the removal of healthcare-related assets from a healthcare facility for the purpose of enabling the assets for a management objective is taught herein. Practical application of the method as taught herein overcomes a deficiency in the field that limits the ability of healthcare facilities to implement tracking technologies on their existing assets. Such healthcare-related assets include but are not limited to surgical instruments, other surgery-related items, or non-surgical items in a healthcare facility. Just a few non-limiting specific examples include surgical instruments, maintenance and operations tools and equipment, trays, carts, measuring devices, monitoring devices, beds, wheelchairs, IV poles or trees, pharmaceutical trays and food trays. Such healthcare facilities include but are not limited to a hospital, ambulatory surgical center, physician office, in-home care, emergency room, triage setting, long-term care facility such as a nursing home or assisted living facility, emergency care setting not related to a facility, such as but not limited to a location associated with a medical emergency or disaster, a medical care facility in a military theater of operation, a medical care facility associated with a place of incarceration, or any other type of facility or setting providing health-related services and procedures to humans and non-humans such as animals. Such management objectives include but are not limited to any number of healthcare facility asset management goals such as inventory control, utilization management, reducing the incidence of retained surgical items, risk management or asset maintenance. Such management objectives also include but are not limited to the synthesis and utilization of data for purposes including but not limited to quantifying, characterizing and managing internal healthcare facility processes, managing the quality of services provided to stakeholders such as patients, optimizing patient satisfaction and outcomes, or for managing relationships with external vendors such as manufacturers or sellers of assets.

The method for coordinating the removal of healthcare-related assets from a healthcare facility is conceived to enable implementation of any means for asset tracking by providing for a healthcare facility's assets, particularly but not limited to existing assets in inventory, to be retrofitted with a durable means of identifying information, such as but not limited to the placement of an RFID chip, without significantly disrupting the healthcare facility's normal operations. As utilized throughout, the terms "durable means of identifying information" and "durable information identifier" are construed to mean the same thing and to be used interchangeably. Further, disclosed herein are a number of instrumentation apparatuses and "measurement apparatuses", of which some may be used for detecting a durable information identifier. Such apparatuses may be described as "durable information identifier detectors". Such uses, along with general terms such as "instrumentation" or measurement sensors, or transducers, are all utilized with the intent to describe apparatuses utilized to quantify or qualify information about assets such as but not limited to a durable information identifier. All such descriptive uses are meant to be non-exclusive, conceptually synonymous and construed to be used interchangeably. Further, the implementation of a means of asset tracking may include steps that physically alter the asset. Such physically altering steps are generally known herein as "manufacturing" processes, steps or phases, and are conceived in the method to preferably take place at a location physically separated from the healthcare facility, also generally known herein as a "manufacturer". Accordingly, the method is also conceived to support manufacturing processes and minimize time needed to complete manufacturing steps performed on the assets.

The method for coordinating the removal of healthcare-related assets from a healthcare facility includes a series of first steps comprising a "pre-processing phase", preferably undertaken at a healthcare facility to prepare each asset for a manufacturing process.

Steps in a pre-processing phase include determining and implementing a first identifier of each asset as an individual unit. For example, asset inventory may include any quantity of a particular surgical instrument. Each instance of the surgical instrument is considered a unit of the asset. Such first identifier would be provided for each unit of the surgical instrument, preferably such that each unit is uniquely identified. Such first identifier may provide the same information as any other unique identifier associated with the unit, such as but not limited to the unique device identifier used with the Global Unique Device Identification Database (GUDID) administered by the United States Food and Drug Administration. Various embodiments of the first identifier may include but are not limited to an alphanumeric number, any form of barcode, any form of data matrix code such as a QR code, a unique graphic image including but not limited to any variety of color-coding means, a temporary RFID chip, RFID substrate or label, or any other means of providing temporary identification. Such first identifier may utilize a temporary means of placement for the purposes of identification through the steps of the method. All embodiments of a first identifier are conceived to be placed on the asset unit and removed at any time advantageously desired in the method. A non-limiting example of such temporary placement includes the use of a barcode sticker or detachable tag.

Further to the pre-processing phase, the determination of each first identifier is made in coordination with a record of each asset unit. Such record may include but is not limited to any form of a written record. In a preferred embodiment, such record is an element of at least one database. Such databases include but are not limited to a database containing characteristic or specification information about the asset type, known herein by the example name of a Master Asset Library (MAL); a database containing information related to the processing of each asset unit in accordance with the method, known herein by the example name of a Universal Processing Database (UPD); and a database containing information about each asset unit as may be utilized by the healthcare facility for asset and process management, also in accordance with the method, known herein by the example name of a Healthcare Facility Information Library (HFIL).

In one embodiment of an MAL database, information determined, recorded or utilized may include but is not limited to the name of the asset, such as the name of a type of surgical instrument or any other type of asset; alternate names for the asset that are known in the art and in the professional field in general; the name and related information of at least one manufacturer of the asset, the part or model number of the asset as associated with the at least one manufacturer, along with any other manufacturer-specific information related to the asset; and at least one graphic image of the asset, such as a standard image file or filename.

In one embodiment of a UPD database, information determined, recorded or utilized may include the first identifier for each particular asset unit processed in the method. UPD database information may also include information contained in an MAL for each particular asset unit, such that UPD information may be embodied as a duplicate of MAL information or may be connected via a relational database link Additional UPD database information may include but is not limited to a unit's GUDID if it is available, the unit's serial number or similar unit-specific information related to its manufacturer or source, such as but not limited to a sales distributor or related entity.

Further to the embodiment of a UPD database and to the practice of the method, information determined, recorded or utilized may include information utilized by a manufacturer for the purposes of at least retrofitting an asset unit with a durable means of identifying information. Such information utilized by a manufacturer may include but is not limited to production related process instructions and parameters, production dates and related information, process control information, tracking and traceability information, regulatory compliance information and quality assurance or quality control information.

In one embodiment of an HFIL database, information determined, recorded or utilized may include any healthcare facility inventory information existing prior to application of the method and more specifically to the pre-processing phase. HFIL database information may also include information contained in an MAL or a UPD for each particular asset type or asset unit, such that HFIL information may be embodied as a duplicate of the MAL or UPD information or may be connected via a relational database links. Additional HFIL database information may include but is not limited to an asset type's allowable substitute or alternate asset types, information about typical use cases for asset types, and at least one location of asset unit inventory.

Further to the method, the HFIL or a similar database is implemented to contain a complete and ongoing record of the life cycle and utilization of assets and asset units. Such record may include information determined, recorded or utilized at every processing step or process utilization of an asset unit over its entire life cycle. Such information may include but is not limited to the processing steps of purchasing an asset unit, maintaining an asset unit, information about the utilization of an asset unit arising from at least one instance of use, information arising from at least one instance of process management in a healthcare facility associated with an asset unit such as the cleansing, decontamination or sterilization of an asset unit, and obsolescence of an asset unit such that it is retired or removed from active use at the end of its life cycle. As such and further to the methods taught herein, a database similar to an HFIL may also be utilized by entities involved in the manufacture, distribution and sale of asset units to healthcare facilities or similar entities, and to entities involved in the removal and subsequent disposal of asset units after the end of the asset units' lifecycle.

Further to the pre-processing phase of the method, at least one asset unit to be retrofitted with a durable means of identifying information, henceforth known as and referred to interchangeably as a "processed unit" or a "processed asset unit", is removed from healthcare facility inventory. A first identifier for the processed unit is determined and implemented by associating the first identifier with the processed unit. In other words, the implementation of a first identifier includes placement of the first identifier on a processed unit. As an alternate embodiment, a processed unit may be placed in an individual container, such as for a non-limiting example a box or bag, and the first identifier may be placed on the individual container. As another alternate embodiment, one or more processed units may be placed in a container, such as for a non-limiting example a compartmented tray, and the first identifier may be placed on the container in a way that associates the first identifier with the correct processed unit. A non-limiting example of one embodiment of this step includes the determination of a barcode providing first identifier information, the printing of the barcode on to an adhesive label, and the placement of the adhesive label on the processed unit such that the label is at least temporarily affixed to the processed unit.

Further still to the pre-processing phase of the method, the first identifier is associated to inventory data for the processed unit. An example of such association is accomplished by appending or adding the first identifier to a database such as but not limited to a UPD or an HFIL, with such adding accomplished through software means. A non-limiting example includes the use of any form of barcode reader known in the art and software configured to acquire the information read by the barcode reader and add the information to a database containing information about the processed unit.

The pre-processing phase may also include a step in which inventory data for assets in the healthcare facility are created if such data do not already exist, particularly but not limited to inventory data as needed to provide information to a UPD to implement the method. The creation step may be done by any means known for the creation of data. In one example embodiment, an operator may present an asset unit to a machine vision system of hardware and software, any example of such system as known in the art, such that the machine vision system can recognize the asset unit by comparison to assets in a database such as an MAL. Upon recognition, software practically applied for the purpose of managing data in the method may extract relevant information from a database such as an MAL and use at least one datum in the creation of inventory data.

The pre-processing phase may also include a step in which at least one graphic image is created of an asset if no such image already exists in a database such as an MAL. Such images are created to specifications and standards as needed to implement the method. Software practically applied for the purposes of implementing the method may create image filenames to follow a standard naming convention, such that once an image is created and named to the standard then the image will automatically link to a database such as a UPD without a further processing step. Such images may be later utilized for purposes such as recognition by a machine vision system and uses in which a human operator may benefit from an image of an asset.

Examples of such human operator uses are disclosed later herein.

The method for coordinating the removal of healthcare-related assets from a healthcare facility for the purpose of enabling the assets for a management objective further comprises a series of second steps implemented in a "removal phase". In the removal phase, processed units of assets that have already been through administration of the pre-processing phase are removed from a healthcare facility and controllably transported to a manufacturing process.

The removal phase is implemented in the method after a first identifier has been placed on or in association with each processed unit to be removed from a healthcare facility. At least one objective in the removal phase is to create and implement a means for tracking and traceability of subsequent steps in the method for purposes including but not limited to complying with laws and regulations, meeting quality assurances, process controls and documenting chain of custody of the healthcare facility assets.

As a typically first step of the removal phase, the first identifier of each processed unit to be removed is appended to at least one database. In a preferred embodiment, the first identifier is a barcode temporarily attached to a processed unit and the first step of the removal phase is implemented by reading the barcode with any form of barcode reader known in the art. Further to the preferred embodiment, software practically applied for the purposes of implementing the method appends the first identifier and related data to a database such as a UPD. Such related data may include but is not limited to the date and time of appending, the identification of the operator performing the appending, the manufacturing process to be applied to the asset and the manufacturer designated in the method to carry out the retrofitting of the processed units with a durable means of identifying information. These steps in the preferred embodiment are repeated for every processed unit to be removed. These steps are also not limited to single asset units. The method is equally applicable to asset units gathered in quantities, such as but not limited to batches of like units, as may be advantageously practiced to implement the method.

The removal phase further comprises a step in which all processed units to be removed are packaged following the step of appending first identifier information to a database.

In a preferred embodiment, such packaging is conceived to facilitate subsequent manufacturing steps. As a non-limiting example of a preferred embodiment, assets may be packaged in a way that each processed unit's temporarily applied barcode labels are positioned to facilitate subsequent reading by a barcode reader.

The removal phase further comprises a step in which documentation and tracking information related to the physical transport of assets from the healthcare facility to the manufacturer designated to carry out the retrofitting is created to implement the method. Such documentation and tracking information may include but is not limited to processed units being removed, information about which processed units are in a particular package, and information about all packages comprising the complete lot (i.e. the totality of all packaged processed units) being removed. Such tracking information is preferably appended to a database such as a UPD.

The removal phase is completed when the complete lot is physically transported from the healthcare facility to the location of the manufacturer designated to carry out the retrofitting to implement the method.

The method for coordinating the removal of healthcare-related assets from a healthcare facility for the purpose of enabling the assets for a management objective further comprises a series of third steps implemented in a manufacturing phase.

As utilized throughout, the term "manufacturing phase" is meant to describe a series of tasks performed by a manufacturer and carried out for the purpose of retrofitting asset units with a durable information identifier to enable assets to achieve a management objective. Further as utilized throughout, the term "manufacturing process" is meant to be construed as any process that retrofits any one or more asset units with an added object or added material, or that alters the appearance of, the structure of, the functionality of, the contents of, of the physical dimensions of any one or more asset units for use in practicing one or more of the methods taught herein. The manufacturing phase may be applied to any number of lots transported to the manufacturer.

In the manufacturing phase, as implemented in the method, at least one lot of healthcare facility assets transported in the removal phase is received at the location of the manufacturer upon arrival. As recited herein, the manufacturer may be located anywhere such as a permanent location of a manufacturing facility or a temporary location of a manufacturing facility such as but not limited to a mobile facility taken to a location advantageously placed with respect to a healthcare facility. As a preferred first step of the manufacturing phase, transported asset lots are received by the manufacturer for purposes including but not limited to verifying the transported assets match corresponding information provided on transportation documentation as created in the removal phase. In a preferred embodiment, the method further comprises a step as needed to reconcile any discrepancies between transported assets and corresponding information provided on transportation documentation.

Further to the manufacturing phase, the asset lot may undergo any number of processing steps associated with being received, such as but not limited to steps that update tracking information in a database such as a UPD or an HFIL. Steps associated with receiving a lot may also include the updating of at least one piece of tracking information independently maintained and utilized by the manufacturer.

Further still to the manufacturing phase, and at the onset of manufacturing processes applied to a processed unit for the purposes of implementing the method, a processed unit's first identifier is introduced to the manufacturing process for purposes including but not limited to enabling manufacturing steps. The introduction of a first identifier may include but is not limited to an operator reading a number, or any means of reading information utilizing "first identifier detector" instrumentation such as measurement devices or sensory readers such as a barcode reader or a device capable of reading transponder information such as an RFID reader. In a preferred embodiment of the method, the introduction of a first identifier is accomplished by reading a barcode temporarily attached in the removal phase as recited herein. Further to the preferred embodiment, the first identifier is introduced to the manufacturing process to provide information about the asset and the processing steps to be subsequently undertaken on the processed unit for the purposes of implementing the method.

In another preferred embodiment of the method, manufacturing processes are carried out for the purposes of attaching or enabling a durable information identifier on each asset unit, such as but not limited to a durable RFID chip to each asset unit. As such, the step of introducing a first identifier to the manufacturing process may further include uses of machine vision. Such uses include but are not limited to capturing an image of a processed unit and processing such image in software practically applied for the purposes of implementing the method. Such processing of an image may provide information for the purposes of verifying the asset's identification as provided by the first identifier. Further, such processing may provide information that identifies a location and orientation of a processed unit for the purposes of enabling physical introduction to at least one manufacturing step. A non-limiting example includes providing location and orientation information to an automated process, such as a robotic device, enabling the automated retrieval and placement of the processed unit to the at least one manufacturing step. Further still, such processing may provide location and orientation information for the purposes of identifying preferred placement and relative orientation information for an object such as an RFID chip to be durably attached to the asset unit. In a preferred embodiment, such purpose is conceived so that the RFID signal resulting from the combination of an RFID chip and the asset unit to which the RFID chip is affixed is either enhanced or optimized for the purpose of subsequent reading by instrumentation such as an RFID reader. Such preferred location and orientation information for an asset is conceived in the method to be included in a database such as an MAL. As such, databases such as an MAL, UPD or HFIL as recited herein may be advantageously utilized by a manufacturer for implementing the method. Further still, such location and orientation information for an asset may be further utilized by a manufacturer to guide at least one manufacturing step that introduces and places an object such as an RFID chip on to a processed unit for the purposes of durable attachment.

Further still to the manufacturing phase, tracking and traceability information related to the implementation of the method is updated. Such updated information includes but is not limited to information identifying any object added to an asset unit, and to any number of manufacturing process steps undertaken in the manufacturing phase. In a preferred embodiment, such information is a unique identifier, such as a serial number, for an RFID chip that has been durably affixed to an asset unit. More specifically to the method, such information identifying an object added to a processed unit is appended to a database such as a UPD or an HFIL, such that the identifying information may be related to the first identifier for the processed unit. As such, the information identifying an object added to a processed unit becomes a second unique identifier for the asset unit. Such second unique identifier information may be added to a database by any means already recited herein, such as but not limited to the scanning of a barcode or the reading of an RFID chip, or may be transferred from any data source containing manufacturer inventory information.

Following completion of all manufacturing processes and steps appending databases containing information such as but not limited to assets, asset units, manufacturing steps and processes applied to processed asset units, information related to manufacturing such as process controls and quality assurance information, tracking and traceability, the manufacturing phase further comprises a step in which all processed units are packaged for return to the healthcare facility. In a preferred embodiment, such packaging is conceived to facilitate subsequent re-introduction to the healthcare facility's inventory and related data systems. As a non-limiting example of a preferred embodiment, assets may be packaged in a way that each processed unit's means of providing either a first identifier or a second identifier is positioned to facilitate subsequent utilization such as but not limited to reading by a barcode reader or an RFID measurement device such as an RFID reader or scanner. With reference to the methods and apparatuses taught herein, the second identifier is preferentially a durable information identifier.

The manufacturing phase further comprises a step in which documentation and tracking information related to the physical transport of assets from the manufacturer back to the originating healthcare facility is created to implement the method. Such documentation and tracking information may include but is not limited to processed units being removed, information about which units are in a particular package, and information about all packages comprising the complete lot (i.e. the totality of all packaged processed units) being removed and returned to the healthcare facility. Such tracking information is preferably appended to a database such as a UPD.

The manufacturing phase is completed when one or more completed lots of assets that have undergone all method-related manufacturing processes is physically transported from the manufacturer back to the originating healthcare facility to implement the method.

The method for coordinating the removal of healthcare-related assets from a healthcare facility for the purpose of enabling the assets for a management objective further comprises a series of fourth steps implemented in a "return phase". The return phase may be applied to any number of lots transported to the healthcare facility from manufacturer following completion of the manufacturing phase.

In the return phase, as implemented in the method, at least one lot of healthcare facility assets transported in the manufacturing phase is received at the location of the healthcare facility upon arrival. As a preferred first step of the return phase, returned asset lots are received by the healthcare facility for purposes including but not limited to verifying the returned assets match corresponding information provided on return transportation documentation as created in the manufacturing phase. In a preferred embodiment, the method further comprises a step as needed to reconcile any discrepancies between transported assets and corresponding information provided on transportation documentation.

Further to the return phase, the second identifier of each processed unit is introduced to a database such as an HFIL. Such step may be enabled by introducing second identifier information to a database such as an HFIL as part of a manufacturing phase. Such step may also coincide with the step of receiving the returned asset lots at the healthcare facility as recited herein. Such step may be done by any means recited herein, utilizing software practically applied for the purposes of implementing the method, such as but not limited to applying at least one manual step done by a human operator or by utilization of measurement instrumentation such as a barcode reader, an RFID chip reader or scanner or any other apparatus conceived to implement the teachings herein.

In a preferred embodiment of the method, each durable information identifier such as an RFID chip applied to each processed unit during the manufacturing phase is detected or measured (also referred to as "scanned" in some cases) in the return phase by at least one apparatus such as but not limited to an RFID reader or scanner implemented at the healthcare facility and utilized for the purposes of implementing methods for managing healthcare assets and processes subsequently recited herein. Further to the preferred embodiment, information received by detecting, measuring or scanning the durable RFID chip, which comprises the second identifier previously recited, is appended to at least one database such as but not limited to an HFIL. This step may include making a comparison between database information associated with a first identifier and information associated with a second identifier for purposes such as but not limited to verifying that asset and processed unit characteristic or specification information about the asset is consistent. Further to the preferred embodiment and the method for coordinating the removal of healthcare-related assets from a healthcare facility, this step is conceived to verify that the means of enabling each healthcare facility asset unit for a management objective as taught herein is functionally operable and capable of facilitating methods for managing healthcare assets and processes subsequently recited herein. In any embodiment, steps taken to assure functional operability may be repeated to establish a statistical indicator of reliability for the asset unit's ability to have at least its second identifier consistently read and utilized to implement the method. Further still to the preferred embodiment, the method further comprises at least one step as needed to reconcile any discrepancies discovered in data comparisons or any lack of functional operability that may be discovered.

Further still, the return phase includes a step in which information is appended to a database such as a UPD for the purposes of updating tracking information on at least one processed unit and closing the associated processed unit processing record associated with implementing the method of coordinating the removal of healthcare-related assets from a healthcare facility. Such information may include but is not limited to the date, time and human operators involved in the return and re-introduction of processed assets to the healthcare facility inventory, and to the closure of the processes to implement the method.

The return phase is completed when all assets that have undergone all method-related manufacturing processes are physically returned to inventory for utilization steps typically carried out at the healthcare facility and for implementing methods for managing healthcare assets and processes subsequently recited herein. The completion of the return phase may also include the step of creating and executing any form of process completion or closure documentation.

Further still to the method recited for coordinating the removal of healthcare-related assets and enabling the assets for a management objective, the first identifier, as conceived to be temporarily affixed to a processed unit, may be removed at any time in the method after the second identifier has been determined and associated with the processed asset, such as but not limited to appending the second identifier to a database.

Further still, the method is not limited to interactions between healthcare facilities and manufacturers for retrofitting assets. The method as recited herein could apply to any other party with interest in the management of such healthcare-related assets. Just one non-limiting example of such party with interest is an original manufacturer of assets. For example, the method as taught herein may be applied when an original manufacturer of assets sends such assets to a third-party manufacturer for processing and retrofitting that enables a healthcare facility management objective. Further to the example, such manufacturer-to-manufacturer interaction may occur prior to the instruments being acquired by the healthcare facility.

Further still, the method may also include a step in which the timing of the removal of one or more healthcare-related assets from a healthcare facility is determined and scheduled in coordination with production scheduling or production capacity availability at the manufacturer. Such step is conceived to minimize the time between the removal phase and the return phase of the method.

Practical implementation of this and other methods disclosed herein for enabling or improving healthcare asset and process management may further involve manufacturing-related steps, methods or apparatuses.

For example, manufacturing processes may include utilizing data from the method for coordinating the removal of assets from a healthcare facility, such as but not limited to the use of the first identifier, to optimize manufacturing processes. A non-limiting example of such includes using the first identifier to segment like-asset units from a lot or a batch. Such segmenting may include physically separating asset units into batches of like units or like assets. Segmented units can then be processed in any number of generally repeating manufacturing steps, thus impacting processing time and related costs in an advantageous way.

Another non-limiting example of utilizing data from the method for coordinating the removal of healthcare-related assets from a healthcare facility in a manufacturing process includes providing data gathered prior to a removal phase and transmitting such data to the manufacturer prior to executing manufacturing steps or processes, also known as pre-production steps. Such could be used to achieve any number of manufacturing-related efficiencies, such as but not limited to preparing equipment or tooling used in manufacturing steps, preparing consumable material or supplies used in a manufacturing process, or preparing human resources for operations carried out in a manufacturing process. Yet another non-limiting example of pre-production use of such data includes use of quantity-related data to allocate manufacturing resources such as equipment, tooling, consumable materials, supplies or human resources. Yet another non-limiting example of the use of quantity-related data includes uses for manufacturing components or subassemblies of components that are used in later manufacturing process steps on the healthcare facility assets. Such manufacturing of components or subassemblies includes pre-production steps and steps that are carried out concurrently to the manufacturing process steps undertaken on the healthcare facility assets. Just one example of such manufacturing of components or subassemblies includes the manufacture of any type of fastener utilized to assist in implementing a durable means of identifying information, such as but not limited to an RFID-chip, on an asset unit.

Another non-limiting example of utilizing data from the method for coordinating the removal of healthcare-related assets from a healthcare facility in a manufacturing process includes enabling the use of machine vision systems for enabling and carrying out manufacturing process steps. A non-limiting example of such includes using data from an MAL such as to compare at least one image of a processed unit undergoing a manufacturing process to images in the MAL for purposes including but not limited to identifying the processed unit, physically introducing the processed unit to a manufacturing process through an automated means, locating the processed unit relative to manufacturing process equipment or tooling, or orienting the processed unit relative to manufacturing process equipment or tooling. Further to the purpose of orienting the processed unit, such use is conceived to support proper placement of any durable means of identifying information, such as but not limited to an RFID-chip, on an asset unit such that the placement aids in post-manufacturing detection and processing of the durable means of identifying information. Such detection and processing may include but is not limited to reading an RFID chip by an RFID scanner or reader.

Such uses related to machine vision systems may also include establishing or recalling parameters related to manufacturing quality controls or process controls, and making a determination of quality or process acceptability.

Further still, all manufacturing data utilized in implementing the method is conceived to be subjected to correlation with post-manufacturing utilization data, such as data gathered in accordance with the method at a healthcare facility, in such a way that utilization data may be adjusted to improve manufacturing processes, such as but not limited to manufacturing efficiency, reliability, quality metrics and asset functionality in accordance with the method. As just one non-limiting example, post-manufacturing utilization data related to asset identification detection or readability may be subsequently utilized in a manufacturing process to adjust or improve the location or orientation of any durable means of identification utilized on an asset or an asset unit. Such adjustment or improvement of location or orientation includes but is not limited to adjusting parameters in a machine vision system.

Figure 2:
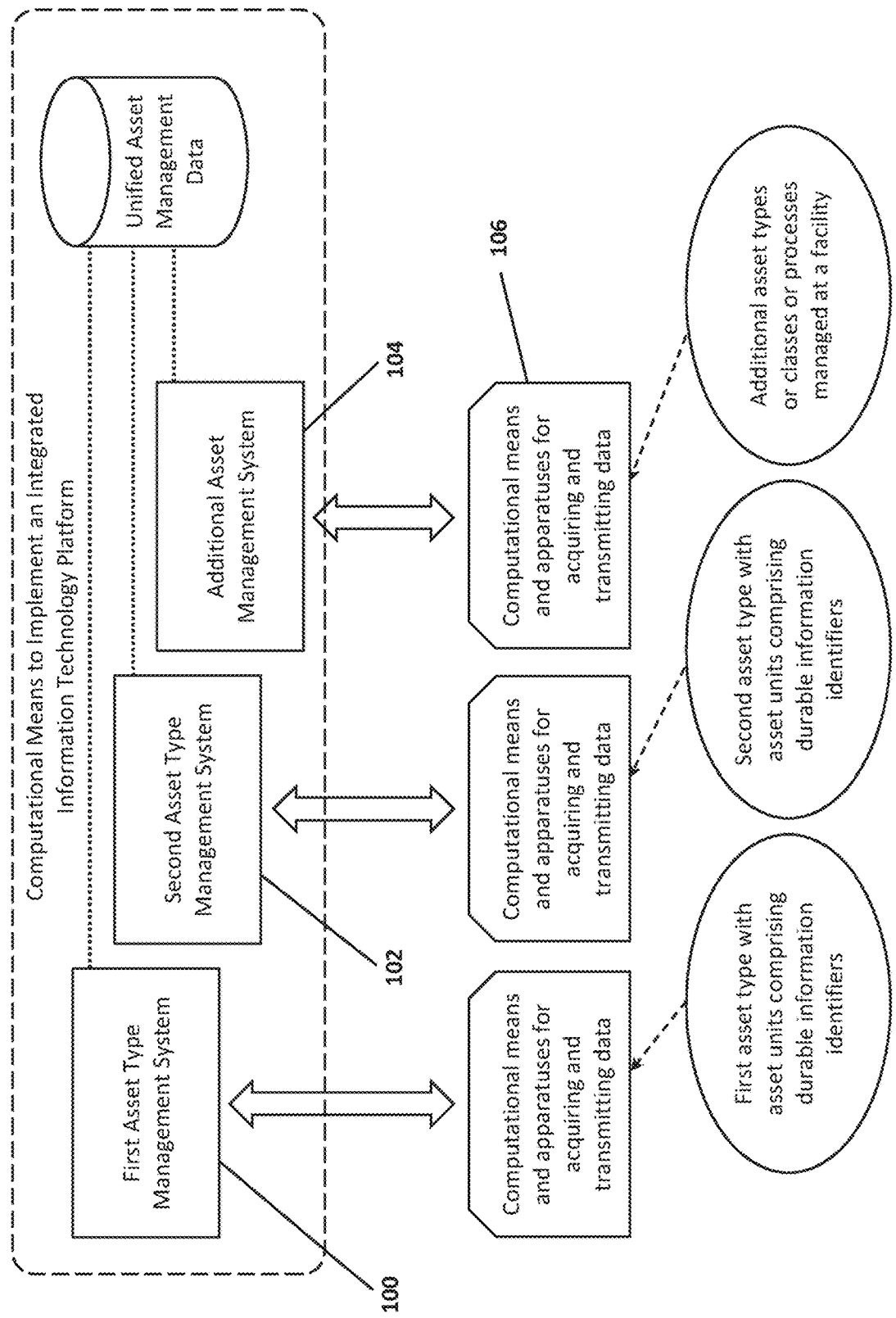

FIG. 2 shows a block diagram of a method and system for the integrated management of healthcare facility assets and uses thereof in healthcare facility process management is taught herein. Practical application of the method and system provides data arising from asset management, correspondence of such data to healthcare facility processes, various means of analyses of such data utilized to quantify healthcare facility processes, and subsequent use of such analyses for purposes such as process management, improvement or optimization.

The integration of healthcare facility asset management is conceived to address a general need in the field in which a multiplicity of otherwise independent asset management systems, each conceived to manage particular types or classes of assets, are related to or controlled by an integrated information technology (IT) platform, structure or system (collectively "IT platform"), operated by one or more computational means that may comprise processors and memory, and are configured to provide asset management data with unified characteristics to the IT platform. Such unified characteristics may be reduced to practice as a common data structure or protocol, thus conceived to provide consistent data from each asset management system, such that the data may be analyzed and utilized for the aggregate of healthcare facility assets.

The method is generally reduced to practice by implementing technologies of a first asset management system 100, a second asset management system 102, or any number of additional asset management systems 104 conceived to manage and track a multiplicity of types or classes of healthcare facility assets (collectively the "asset management systems"). Such asset management systems may comprise instrumentation 106 such as computational means and apparatuses for acquiring and transmitting data associated with at least one asset or asset unit. The method preferably comprises asset management systems for a multiplicity of asset types or classes to be tracked and managed. Further to a preferred embodiment, subsequent management systems or management technologies for additional types or classes of assets may be added to the system at any later time following initial implementation of the method, particularly as determined to be advantageous to the healthcare facility.

Instrumentation 106 utilized to implement the method as taught includes but is not limited to devices for measuring characteristics of asset or asset unit use, such as detecting the presence or location of at least one asset unit, detecting the quantity of an asset or asset unit, or quantifying a physical characteristic of an asset or asset unit. The method is preferably implemented utilizing assets and asset units that feature and utilize at least one form of durable means for providing identifying information as taught herein, with such means more preferably being capable of operably interacting with instrumentation 106 used to implement the method.

Further to the method, instrumentation 106 for quantifying or qualifying asset use is provided in proximity to locations where any number of healthcare facility process functions or processing procedures take place, or in association with the process functions or processing procedures. Examples of such locations or functions include but are not limited to examination rooms, patient hospital rooms, medical procedure areas such as surgical operating rooms, locations where health-related therapy is applied, locations where assets undergo cleansing, decontamination or sterilization, locations or functions involving the maintenance of assets, locations or functions involving the dispensing of at least one pharmaceutical, or locations or functions involving healthcare facility administration. In a preferred embodiment, instrumentation 106 is located in proximity to or in association with all healthcare facility process functions for which a management objective includes the management of the process functions. Further still, instrumentation 106 may also include any devices or means utilized in a healthcare facility for purposes known in the art as "real time locating systems" (RTLS), and the method for integration of healthcare facility asset management may include integration of instrumentation 106 and data associated with an RTLS.

Further still, the method is implemented when any combination of any number of instruments used for quantifying or qualifying uses of at least one type or class of asset in a healthcare facility is provided, and the instruments in the combination are operably coupled via at least a means of either receiving data from or transmitting data to an IT platform configured to provide asset management data with unified characteristics and implemented for integrated healthcare facility asset management. The method is preferably drawn to the integration of various means for managing multiple types or classes of assets.

Further still, the method is not limited to data acquired by or transmitted from instrumentation 106 integrated to an IT platform operated by one or more computational means that may comprise processors and memory. For example, additional data utilized for the purposes of integrated healthcare facility asset management may include any data relevant to the method manually acquired by a human operator, whereby at least one datum acquired by the human operator is entered into an IT platform for integrated healthcare facility asset management.

Further still, data associated with the method are not conceived to be limited to such data associated with healthcare facility assets. Additional bodies of data may include measures or characteristics of human activity or experiences. Numerous examples are conceived, and include but are not limited to data associated with the tracking of healthcare facility employees and related human resources. Other examples include data associated with the tracking of patients including but not limited to measures or characteristics of patient experiences and outcomes. Such data and uses are further taught herein. Other examples also include data associated with either human resources or processes arising from ancillary support of a healthcare facility. Such ancillary support may be embodied by third-party functions such as but not limited to external vendors such as manufacturers or sellers of assets; healthcare providers associated with a patient such as but not limited to a physician, nurse, or other professional caregiver not directly affiliated with a healthcare facility; and non-professional supporters of a patient such as a family member, a guardian or any other form of collateral support caregiver.

The method further comprises steps of determining and implementing a data protocol that enables an integrated asset management system as taught herein. Such data protocol may be consistent with any number of such means known in the art, provided it is conceived to provide a consistent and standardized means to implement the method. The method is further implemented when instrumentation 106 for quantifying or qualifying asset use is configured to either receive or transmit data utilizing a standard data protocol. The method is further implemented when any other measurement means of either providing or acquiring data relevant to the method utilizes the standard protocol. In a preferred embodiment, the standard protocol is conceived to achieve data security objectives and compliance to regulations such as but not limited to the Health Insurance Portability and Accountability Act (HIPAA) in the United States.

The method is further implemented when standardized data associated with a healthcare facility asset includes data such as but not limited to the asset's name, class, physical characteristics or specifications, manufacturers, approved vendors, use cases, alternates for use, dates or individual names associated with healthcare facility introduction and utilizations for each asset unit, records of healthcare facility process steps applied to each asset unit, maintenance parameters, maintenance records applied to each asset unit, quality records related to each asset unit, corrective or preventive actions applied to an asset or asset unit, or expected life cycle.

The method further includes steps of creating and operating an IT platform that manages instrumentation 106 and related means of data acquisition, and is configured to achieve, detect and maintain operability of such instrumentation 106 and means of data acquisition in an integrated system. In one non-limiting example of a method for detecting and maintaining operability of instrumentation 106, software practically applied in an IT platform may periodically transmit at least one first datum such as a control code to at least one instrument in an integrated system. Such periodic transmission may preferably occur at least once each day, more preferably may occur at least once each hour, and more preferably may occur at least once each 1-5 minutes. The software may be further configured to receive back to the IT platform at least one second datum transmitted from the at least one instrument in response to the initially transmitted first datum. Such response is sometimes known in the art as an instrument's "heartbeat". Such second datum may be configured to indicate information including but not limited to confirmation that the first datum was received successfully, confirmation that a command intended to influence or alter a state of the instrument was received by the at least one instrument and such influencing or altering of a state was carried out successfully, or information configured to indicate that the at least one instrument is functioning normally or as expected. This aspect of the method also contemplates a step in which an unsuccessful transmission of at least one datum and receipt of a second datum, such as a missed heartbeat, triggers at least one response mechanism to resolve a related operational failure. Such response mechanisms may include but are not limited to initiating an automatic corrective action, such as a software routine practically applied to resolve functional failures, or a response from a human operator conceived to resolve functional failures.

The IT platform further comprises means of interfacing to instrumentation 106 and any other means of data acquisition implemented to achieve the method. Such means of interfacing may be implemented through any number of wired or wireless means known in the art. Software may be practically applied in the IT platform to acquire data from the various instruments or related means of data acquisition, and may further be configured to consolidate, process and store acquired data for subsequent use by at least one or more software applications practically applied to implement the method of integrated healthcare facility asset management or process management. In a preferred embodiment, such storing of data includes the use of databases configured for storing integrated asset management data, and may include the use of or consolidation of data contained in databases including but not limited to an HFIL, UPD or an MAL. Further still, the IT platform is preferentially configured to interface with and integrate to a healthcare facility's electronic medical records (EMR) system.

As noted, the method of integrated healthcare facility asset management contemplates use of at least one integrated software application that is determined, implemented and practically applied for purposes taught herein. Such software is conceived to reduce the number or variety of independent software applications used for asset management or process management in a healthcare facility. Such helps beneficially address a problem known in the art and the healthcare field in which healthcare IT management functions are challenged to maintain complex IT platforms and meet requirements such as but not limited to data security and regulatory controls while a wide variety of different software applications are utilized and operate under the same IT platform.

Further, the method contemplates additional software interfaces associated with the IT platform taught herein to implement the method to any number of third-party IT platforms for asset management. Such interfaces to third-party IT platforms may be used to either acquire data from or transmit data to such third-party asset management systems. Such interfaces to third-party IT platforms may be reduced to practice through any means commonly known in the art. In a preferred embodiment, data transmitted through such interfaces to third-party IT platforms follows a common data structure or protocol such as that taught herein, or alternately uses any means of translating or reformatting data that does not follow a standard protocol as taught, such that the non-standard data may be used for purposes of implementing the method. A non-limiting example of such use is to cause non-standard data to be migrated either to or from databases for storing integrated asset management data as taught herein.

As recited and implemented, a method for integrated healthcare facility asset management is achieved. In one non-limiting example of such integrated asset management, the method is reduced to practice when the operation of a system for tracking and managing the utilization and life cycle of surgical instruments in a healthcare facility is integrated to a like system for tracking and managing aspects such as the utilization and life cycle of other assets commonly used in a surgical setting. Such utilization of assets includes but is not limited to one or more process steps performed on an asset or asset unit in a healthcare facility. Such integration includes but is not limited to the operation of apparatuses utilized to achieve the methods taught herein, such as but not limited to instrumentation 106 for acquiring and transmitting data associated with at least one asset or asset unit. Such integration also includes but is not limited to operation of the apparatuses by any form of information technology platform, including but not limited to one or more computational means that may comprise processors and memory, and to any data arising from the information technology system platform. Such other assets include but are not limited to surgical sponges, gauze, equipment used to manage assets in a surgical setting such as trays, carts and baskets, implantable medical devices, pharmaceutical agents utilized in a surgical procedure, or items belonging to the patient and temporarily held in custody of the healthcare facility.

In another non-limiting example, an integrated system for tracking and managing the utilization and life cycle of traditional surgical instruments and other assets used in a surgical setting may be further integrated with a like system for tracking and managing assets implemented in a robotic surgery system. Such robotic surgery system assets may include but are not limited to surgical instruments configured to operably couple to a robot and to other equipment or maintenance parts associated with a robotic surgery system. As used herein, the term "robot" refers to any form of automated or semi-automated device utilized for effecting motion or transferring forces or torques. Further still, an integrated asset management system may also include a system for tracking and managing the utilization and life cycle of durable equipment such as but not limited to endoscopes, bronchoscopes, arthroscopes, laparoscopes, cryosurgical instruments, endocavitary probes, just to name a few. Further still, an integrated asset management system may also include a system for tracking and managing the utilization and life cycle of durable equipment in a non-surgical healthcare setting. Such equipment may include but is not limited to equipment in examination rooms, patient hospital rooms, medical procedure areas such as operating rooms, or locations where health-related therapy is applied. Such equipment may also include equipment not directly related to delivering care, such as but not limited to maintenance equipment and food supply equipment. Further still, an integrated asset management system may also include a system for tracking and managing the utilization of at least one pharmaceutical agent used in a healthcare facility, particularly in relation to a patient being treated at a healthcare facility. Further still, an integrated asset management system may also include a system for tracking patient experiences, or any patient-related metrics including but not limited to symptom metrics or biometrics such as vital signs, where such patient data is acquired at any time before, during or after an interaction with a healthcare facility. Further still, an integrated asset management system may also include a system for tracking and managing tissues or any asset associated with the utilization of at least one biological tissue, such as but not limited to a container of a tissue such as a container for an organ transplant.

Further still, a preferred embodiment of the method is achieved when the healthcare facility's integrated asset management system is further integrated to the product management system of suppliers of original equipment that is being managed in the healthcare facility's integrated asset management system. Such suppliers may include but are not limited to original equipment manufacturers or the vendors of the original equipment. In just one non-limiting example of the utility of such embodiment, a healthcare facility's integrated asset management system may be further integrated to the product management system of a supplier of surgically implanted devices utilized in the healthcare facility. Such surgically implanted devices may include but are not limited to electronic devices, monitors, orthopedic devices, joint replacements, implantable devices for administering at least one pharmaceutical, dental implants and devices or materials related to implanted tissues, including implanted tissues. In just one non-limiting example of the utility of such integration, a healthcare facility's integrated asset management system is further integrated with the product management system of a supplier of orthopedic devices such as but not limited to joint replacements. In a preferred embodiment of the example, the supplier may also provide devices related to the implementation or use of the orthopedic devices, such as but not limited to surgical instruments utilized in an implantation procedure. In another preferred embodiment of the example, the supplier's equipment includes any form of durable means of identifying information as taught herein and as compatible with instrumentation 106 for quantifying or qualifying asset use or any other means of data acquisition utilized in the healthcare facility's integrated asset management system. Thus, the supplier's equipment may be readily utilized in the healthcare facility's integrated asset management system.

The utility and benefit of integrating a healthcare facility's integrated asset management system with the product management system of a supplier is realized in a number of ways. For example, suppliers of orthopedic devices often provide their products in the form of a kit that includes at least one orthopedic device and at least one surgical instrument utilized in an implantation procedure. In many cases, some of the elements of such kit remain the property of the supplier and are intended to be returned to the supplier after utilization in an implantation procedure. Such elements may include at least one orthopedic device in a kit that is preferentially not utilized in an implantation procedure, or rejected for quality control purposes. Such elements may also include surgical instruments that remain the property of the supplier. The integrated asset management system may be utilized to track processing steps and uses of the elements of such kit, including steps applied to the at least one surgical instrument utilized in an implantation procedure and the disposition of the at least one orthopedic device. Such tracking may take place before, during or after an implantation procedure. Such tracking may be utilized for purposes such as but not limited to assuring correct implantable devices are being implanted in an individual patient, and assuring that those elements of a kit that remain the property of the supplier are properly processed and returned to the supplier after the kit is used in a procedure. These and a number of other uses and benefits are readily understood by persons skilled in the art such as healthcare professionals.

The utility and benefit of the method is further realized when a healthcare facility's integrated asset management system is further integrated to healthcare facility management systems for purposes such as but not limited to supply chain functions including purchasing, inventory control, asset maintenance and asset disposition; and to quality management systems such as systems for risk management and mitigation, systems for determining at least one quality metric; and to systems for optimization such as but not limited to systems for minimizing process steps applied to an asset unit, systems for detecting optimal use cases for an asset and systems for minimizing costs. In yet another example, the utility and benefit of the method is further realized when a healthcare facility's integrated asset management system is further integrated to at least one information system utilized by a healthcare professional for purposes associated with the healthcare facility. In a non-limiting example of such, a healthcare professional such as a surgeon or at least one of a surgeon's staff members may utilize an information system integrated to a healthcare facility's integrated asset management system for purposes such as providing information or instructions associated with a patient or a procedure. Such instructions may include transmitting preferences from the healthcare professional to the healthcare facility for the utilization of healthcare facility assets associated with such patient or procedure, or for other attributes of a procedure of healthcare facility uses such as scheduling and coordination of process flows and related asset uses. These and a number of other uses and benefits are readily understood by persons skilled in the art such as healthcare professionals and healthcare administrators.

The utility and benefit of the method is further realized when a healthcare facility's integrated asset management system is implemented at any number of processing points or functions associated with the healthcare facility, whether integral to the healthcare facility or as part of processing points provided by third-parties independent of the healthcare facility. Such processing points or functions may include but are not limited to asset receiving, asset acceptance processes such as verification and validation, introduction to asset inventory systems, inclusion in asset storage, introduction to asset RTLS, asset maintenance functions, asset financial management or accounting, asset cleansing, decontamination and sterilization, asset disposition, and to processing at points of use such as an operating room or like location for the application of procedures, therapies, diagnostics or general examinations.

In just one example of utility at processing points or functions, a healthcare facility's integrated asset management system is implemented as part of processes commonly known and often departmentalized under the name "central sterile processing department" (CSPD). This is a highly important function in healthcare facilities, as CSPD is responsible for a number of management and processing aspects related to assets before, during and after utilization in a procedure or similar healthcare facility process. In just one example of processing before a procedure, CSPD is responsible for gathering and preparing asset units such as surgical instruments to be used for a particular surgery. In an example of processing during a procedure, CSPD is responsible for rapid response to asset-related needs that may arise during a surgery. In an example of processing after a procedure, CSPD is responsible for asset unit cleansing, decontamination and sterilization, all of which are conceived to minimize risks associated with residual contaminants such as biomaterials, pathogens and other infectious agents.

In accordance with the method, at least one instrumentation 106 apparatus or sensor for quantifying or qualifying asset use or any other means of data acquisition utilized in the healthcare facility's integrated asset management system is placed at processing points in a CSPD. Such instrumentation 106 may be utilized to quantify or qualify asset utilization at such processing points, particularly for the purpose of appending a database such as an HFIL with tracking information pertaining to an asset unit and its life cycle in the healthcare facility. In a preferred embodiment, instrumentation 106 located at CSPD processing points includes but is not limited to RFID readers or scanners, and assets processed by a CSPD are configured to include an RFID chip as a durable means of identifying information. The healthcare facility's integrated asset management system is configured to acquire information and data from at least one instrumentation 106 apparatus located at CSPD processing points. Thus, information about asset utilization in a CSPD may be gained at the individual asset unit level each time an asset unit is detected by the CSPD-located instrumentation 106, data related to that detection is appended to a database such as but not limited to an HFIL, and software practically applied to implement the method provides any number of measures, analyses or reports practically used for asset management. Similar uses are conceived for instrumentation 106 placed in operating rooms and other processing points as recited herein. Uses of such instrumentation 106 for process management purposes are later taught herein.

The method as accomplished and implemented provides numerous asset-specific benefits that include but are not limited to opportunities for healthcare facilities to minimize costs, minimize processing steps and time, reduce errors, prevent "never events" such as retained surgical instruments or related materials, reduce institutional risk profiles and reduce healthcare professional risk profiles. The non-limiting examples recited are provided only to illustrate the breadth of the method. They are not limiting in any way, nor do they imply exclusion of the integration of any other asset class, system of management or utilization in a healthcare facility or setting.

Figure 3:
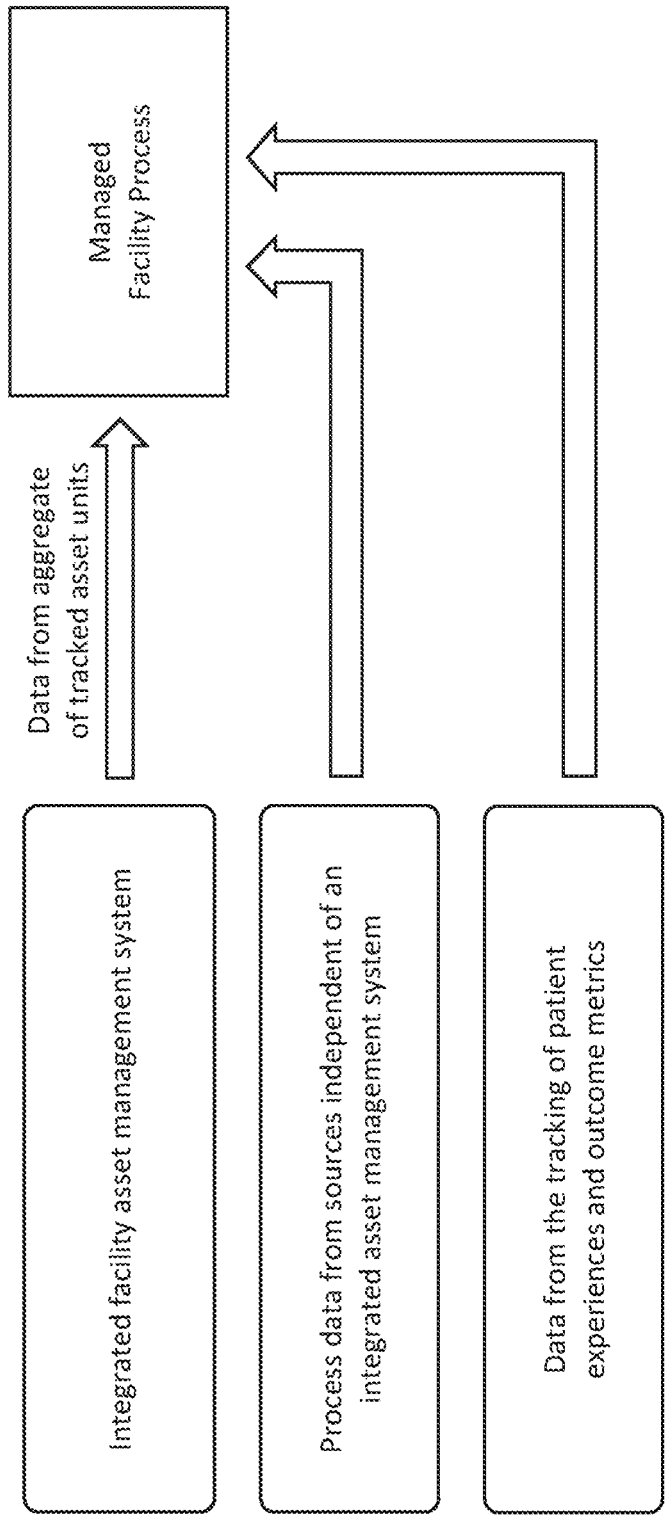
FIG. 3 shows a block diagram of method steps for healthcare facility process management.
Figure 4:
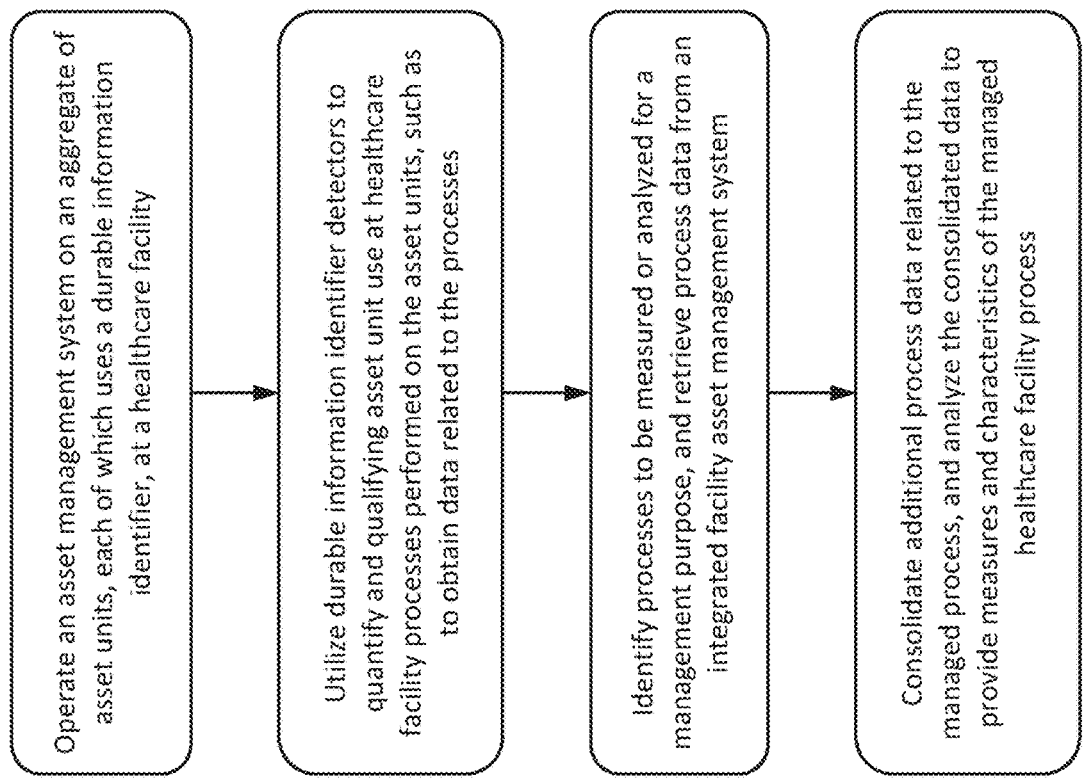
FIG. 4 shows a block diagram of method steps for healthcare facility process management.

FIGS. 3 and 4 show block diagrams of a method whereby tracked assets are used as a means to measure, quantify, qualify or analyze healthcare facility processes is taught herein. For clarity, uses of the methods recited thus far have contemplated the benefits of tracking assets for gaining data pertaining to asset unit life cycles in a healthcare facility, and uses of such data with respect to asset management. When an asset unit comprises a durable means of identifying information, such as means taught herein, the means becomes a sensor that is utilized by instrumentation 106, also taught herein, for quantifying or qualifying asset use. In differentiation, the method further contemplates the aggregate of a plurality of assets, such as entire classes of assets or entire inventories of assets, each unit of which comprises durable means of identifying information. The method as taught uses the aggregate as a means of measuring, quantifying, qualifying or analyzing healthcare facility processes. As such, the aggregate becomes sensors of healthcare facility processes and a method for healthcare facility process management utilizing an integrated healthcare facility asset management system may be realized. The benefits of such healthcare facility process management are readily understood by persons skilled in the art such as healthcare professionals and healthcare administrators.

The method includes a step in which at least one healthcare facility process to be measured or analyzed for a management purpose is identified. Data to be utilized for such managed process is preferably retrieved from data in an integrated healthcare facility asset management system as taught herein. Such data to be utilized may include a body of data related to the managed process and comprising data arising from an aggregate comprising a multiplicity of asset units and asset classes in a healthcare facility asset management system. The method as implemented may include steps in which such body of process-related data is retrieved from at least one database such as but not limited to an HFIL, and is consolidated to be analyzed in relation to a managed process. The method may also include retrieving and consolidating additional data related to a managed process, such as data that may come from sources independent of an integrated healthcare facility asset management system. Such sources may include independent software applications or non-software process functions that may provide process metrics or characteristics.

The method includes further steps of analyzing consolidated data related to a managed process, including but not limited to the body of integrated healthcare facility asset management data as recited herein, in ways that may be subsequently utilized to measure characteristics, such as quantitative and qualitative characteristics, of a managed process. Such analyzing step may be accomplished by software practically applied to achieve the method.

In just one non-limiting example, provided to illustrate the differentiation and utility of this method, a managed process includes healthcare facility processes for sterilizing assets and asset units such as but not limited to surgical instruments or similar durable equipment. Managed process metrics of interest, that may be determined using software practically applied for such purposes, may include but are not limited to the time that elapses between completion of asset use (in any asset grouping including asset units) in a prior process and introduction of the asset grouping to a next managed process such as a sterilization process, times related to asset periods of inactivity, the time needed to complete the managed process on the asset grouping; variability of times associated with the managed process; segmentation of process timing metrics by parameters that may include but are not limited to individual facility sites, different human operators, different healthcare facility timeframes such as operational shifts, different support staff, different assets, different asset classes, different asset suppliers, asset ages or duration of service in a healthcare facility. The managed process metrics may further be quantified by any number of descriptive statistics commonly known in the art. Said statistics may be utilized by healthcare facility personnel, including but not limited to administrative personnel, to quantify or qualify a managed process in ways such as but not limited to means, medians and modes of measures, measures of consistency or variability, identification of statistical outliers, trends related to process execution, or trends related to process quality metrics.

The method, and in particular any aspects of the method utilizing data, is not limited to implementation in a single healthcare facility. The teachings extend to any multiplicity of healthcare facilities, including but not limited to more than one healthcare facility comprising a grouping of healthcare facilities under the same management, a multiplicity of healthcare facilities providing similar or like care, a multiplicity of healthcare facilities providing care to a similar or like patient demographic, or a multiplicity of healthcare facilities in a geographic region. The teachings related to data utilized at least one managed process may be further realized by creating any combination of data from any multiplicity of healthcare facilities, and any utilization of such combination of data.

As such, the examples provided illustrate how measurement of asset utilization and movements tracked as part of an integrated asset management system as taught herein can yield metrics of interest to managed processes, thus implementing the method of healthcare facility process management and yielding opportunities for improving healthcare.

In addition to surgical instruments, and in a preferred embodiment, the method of healthcare facility process management is further realized when integrated asset data includes data arising from other integrated tracking and measurement systems such as but not limited to RTLS, maintenance and operations tools and equipment, trays, carts, baskets, measuring devices, monitoring devices, beds, wheelchairs, IV poles or trees, pharmaceutical trays and food trays. In a further preferred embodiment, the method also includes the tracking and use of pharmaceuticals and devices for providing therapies, diagnostics or general examinations. In yet another preferred embodiment, the method also includes data arising from the tracking of healthcare facility employees and related human resources in relationship to performing a managed process.

In yet another preferred embodiment, the method also includes data arising from the tracking of patient experiences and outcome metrics. Such data may arise from any means of patient monitoring occurring either before, during or after an interaction with a healthcare facility. Such monitoring may occur on a singular or periodic basis. Such monitoring may be utilized to quantify or qualify patient status or experiences in relation to a health condition, and in particular to a health condition related to the interaction with a healthcare facility. Such patient status or experience data may include but is not limited to measures of patient symptoms, condition-related biometrics, vital signs, patient compliance to therapy, patient compliance to instructions related to healthcare facility processes, sleep characteristics and quality, adverse events, adverse events in relationship to a therapy, satisfaction with care, satisfaction with quality of life, outcomes of lab testing including but not limited to medication monitoring tests and analyses of serum such as blood, urine or saliva as is commonly known in the art, correlates to concomitant conditions and behavioral health correlates to a related health condition. For clarity, behavioral health correlates may include but are not limited to measures of mood, cognition, behavior, or any other measurement construct or measure of a functional domain associated with a patient that may be concomitant to any physical condition of which a patient experiences.

Such monitoring and tracking of patient experiences and outcome metrics is conceived to provide various means of identifying relationships between healthcare facility processes and patient outcomes, and to provide opportunities to improve said processes or overall patient outcomes and quality of care by identifying those processes and process characteristics that correlate to the outcomes and quality of care, thus further realizing the benefit of the method. In addition to providing information to an integrated system for managing healthcare assets and processes, such monitoring and tracking of patient experiences and outcome metrics may be configured for further use to alert healthcare facility personnel when a patient is not experiencing expected outcomes of a therapy or procedure, thus providing healthcare facility personnel an opportunity to proactively respond to suboptimal outcomes and consider further intervention.

Such monitoring and tracking of patient experiences and outcome metrics before, during or after a therapy or procedure, including monitoring and tracking that takes place over a period of time before or after interaction with a healthcare facility, may be achieved by any means including but not limited to the use of a software application configured for remote self-monitoring and practically applied to gather and transmit such experience and outcomes data to an integrated system for managing healthcare assets and processes as taught herein. Such software application may be reduced to practice as an internet application, as a mobile application or via any other means known in the art. Transmission of data may be achieved through any operational means of data coupling between such software application and at least one database in an integrated system for managing healthcare assets and processes.

Further still, such monitoring of patient status or experience, and resulting data of the monitoring, may arise from instruments and devices operatively coupled to a patient while interacting with a healthcare facility. In addition to numerous such monitoring instruments or devices routinely used in the art, such monitoring of patient status or experience may also include the use of at least one sensor or transducer device, a non-limiting example of which may include a wrist band or ankle band comprising an RFID chip or similar sensor or transducer configured to be worn by the patient, and a means of detecting or measuring said RFID chip or similar sensor or transducer means.

In just one example of application as implemented in the method, the means of detecting or measuring an RFID chip or similar sensor or transducer is implemented in proximity to locations utilized by a patient while in a healthcare facility, and is configured to detect patient presence and movements associated with the locations. In a non-limiting example, an RFID scanner may be located in proximity to the bed of a patient in a healthcare facility, and the patient may be wearing an RFID band on his or her wrist or ankle. In addition to providing information to an integrated system for managing healthcare assets and processes, such monitoring technology may be configured for further use to alert healthcare facility personnel when a patient is getting out of bed, and providing opportunity for preventive intervention to reduce the risk of the patient falling.

In yet another preferred embodiment, the method also includes the integration of process data associated with the tracking of materials designated for disposal. Such materials include but are not limited to obsolete assets or asset units, pharmaceuticals, used supplies and healthcare-related waste. In yet another preferred embodiment, the method also includes the integration of process data with the product management systems of third-parties such as but not limited to original equipment manufacturers and suppliers. Such integration is conceived to provide means of further improving supply chain management and processes, and processes associated with business relationships between the healthcare facility and the supplier. In just one non-limiting example, data associated with a process utilization of an asset or asset unit may be compared to data associated with the manufacture of the asset or asset unit. Such comparison may yield any number of findings that reveal positive relationships between a manufacturing aspect and a healthcare facility process. For example, consider a segment of asset units found to perform better or yield better operator performance than other asset units in a process utilization, where all such asset units come from the same manufacturer. The better performing asset units may be found to correlate with a differentiated manufacturing aspect such as, but not limited to, a differentiated manufacturing process, a differentiated handling process, a differentiated quality control process or a differentiated selection of materials.

The benefits of the method are further realized when methods of the integrated system for managing healthcare assets and processes include the use of software practically applied to accomplish and report on any number of means, such as but not limited to analyzing at least one process adjustment arising from data or analyses associated with process metrics, and making comparison to pre-adjustment metrics for the purposes of quantifying or qualifying process improvement or the lack thereof; determining at least one correlation between data related to a first managed process and data related to at least a second managed process, such that relationships in which process characteristics of one managed process may be shown to influence process characteristics of at least one other managed processes; determining at least one correlation between process data associated with a healthcare facility and the process data of at least one other healthcare facility in a population of like healthcare facilities, for purposes such as but not limited to making benchmark comparisons of process performances between a healthcare facility and at least one other comparable healthcare facility; determining at least one correlation between process data associated with at least one human operator, such as but not limited to a care provider in a healthcare facility and the process data of at least one other human operator in a healthcare facility, preferably drawn from a population of like operators in a healthcare facility, for purposes such as but not limited to making benchmark comparisons of process performances between comparable operators in a healthcare facility; and determining at least one measure of healthcare facility process characteristics in relationship to any number of socioeconomic measures or statistics associated with the population of persons for which the healthcare facility serves.

The benefits of the method are further realized still when software is practically applied to provide for documenting healthcare facility process steps, particularly to assure appropriateness of care and provide a record such as may be used to comply with risk management needs, defend against litigation, reduce a healthcare facility's overall institutional risk profile, meet regulations and provide related documentation.

Figure 5:
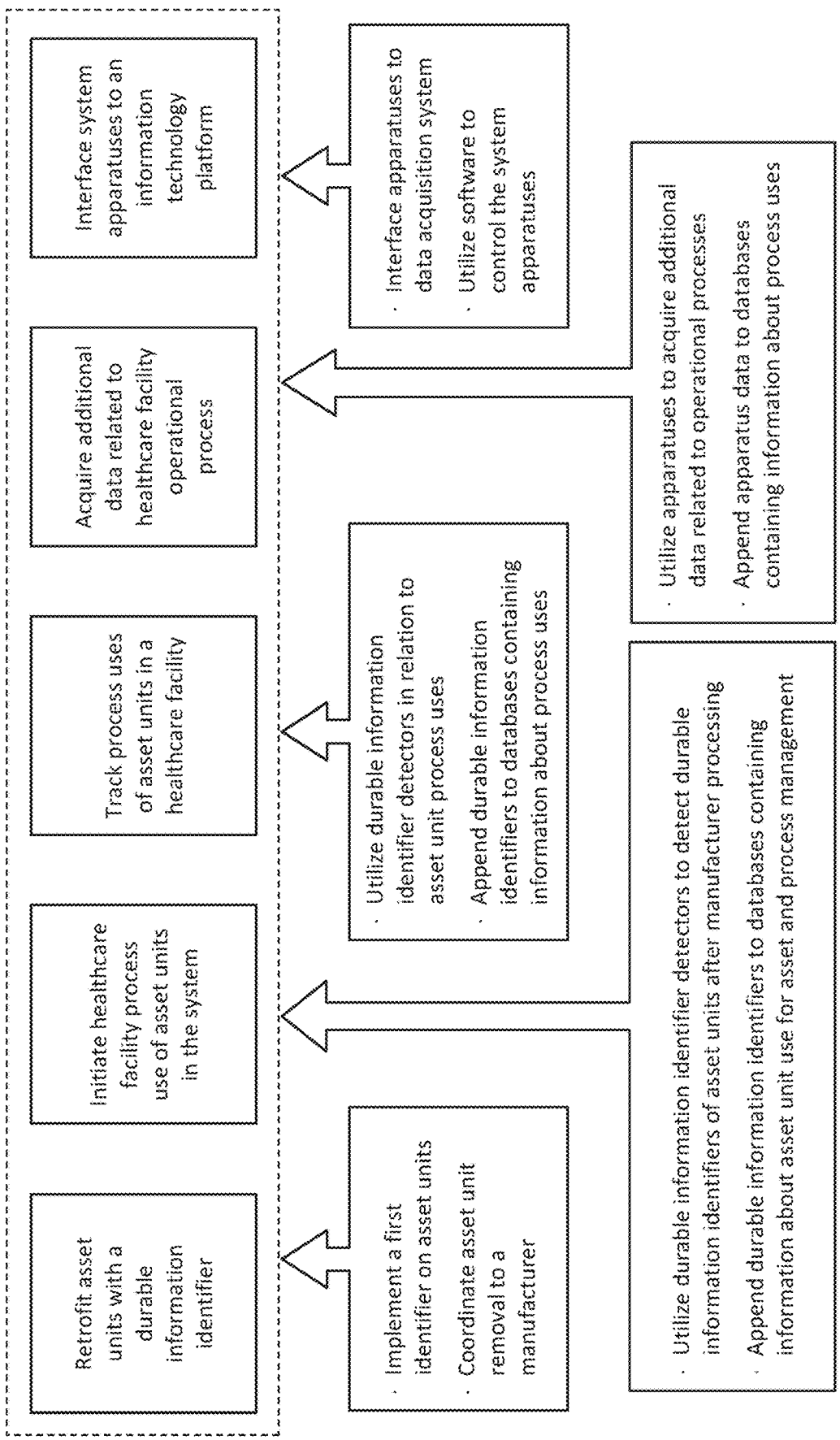
FIG. 5 shows a block diagram of a method for managing assets and healthcare facility processes.

FIG. 5 shows a block diagram of a method for managing assets and healthcare facility processes. Embodiments of the methods disclosed herein may be accomplished by utilizing a number of apparatuses for purposes such as but not limited to instrumentation for acquiring and transmitting data associated with at least one asset or asset unit, including instrumentation configured to detect or measure a durable means of identifying information, or including instrumentation configured to detect any physical attribute of at least one asset or asset unit. Examples of such instrumentation have been recited herein, such as barcode readers and RFID readers or scanners. However, the methods recited herein are not limited to utilization of any particular form of instrumentation in accomplishing their purposes and inventive aspects.

The method may be implemented through any form of instrumentation apparatus configured to detect quantitative or qualitative aspects of an asset or asset unit. Such aspects include but are not limited to the presence, location or quantity of an asset or asset unit. In preferred embodiments, instrumentation apparatuses are configured to detect or measure a durable means of identifying information utilized with an asset unit. Instrumentation apparatuses utilized in implementing the method may also include any devices configured to acquire measures, information or any other data related to at least one healthcare facility operational process.

Further to the method, apparatuses utilized may be operationally coupled to a data acquisition system via any means of wired or wireless interface methods known in the art, and are preferably interfaced to an IT platform utilizing a computer-based data acquisition system that is linked to at least one database. The method may be implemented using computer-based systems including but not limited to computers that may comprise processors and memory, displays and peripheral devices that are integrated with the apparatus or that are implemented as devices physically separated from the apparatuses. Apparatuses may also utilize any number of signal conditioning methods known in the art for purposes including but not limited to improving the quality or integrity of at least one signal, such as but not limited to an electric signal, that is produced by the instrumentation as a result of detecting a quantitative or qualitative aspects of an asset or asset unit. Such uses of signal conditioning methods are conceived to improve the accuracy of various instrumentation apparatus measures arising from the methods.

Apparatuses may provide for passive use, in which detection or measures of an asset or asset unit are achieved without any unit-specific presentation required to function. An example of such passive apparatus is an RFID reader, which is capable of detecting an RFID chip at any location or orientation within the RFID reader's operable field or envelope of operation. Apparatuses may also provide for active use, in which detection or measures of an asset or asset unit are typically only achieved through a purposeful operator interaction. An example of such active apparatus is a barcode reader, which is generally capable of detecting a barcode only after the barcode has been presented to the operable field or envelope of operation of a barcode reader in such a way that the barcode is "visible" to the optical sight of the barcode reader.

Apparatuses may be embodied and utilized in any number of physical manifestations including devices that are handheld or moved by hand to articulate with a measured aspect such as to detect any quantitative or qualitative aspect of an asset or asset unit; devices that are mobile, devices that are fixed on rigid bases such as walls, ceilings or floors; devices that are functionally integrated with fixtures utilized for healthcare facility operations such as but not limited to tables, platforms, cabinets, storage containers, disposal containers; or devices that are functionally integrated with healthcare facility operations such as but not limited to functions that deliver a procedure to a patient, functions that house a patient such as a patient room, functions that support a patient stay, functions of a CSPD or functions associated with asset laundry.

Apparatuses utilized in the method may also be functionally coupled with at least one application of software used to practice the method. Such software may be configured to acquire or transmit data from or to instrumentation utilized for at least one measure associated with an asset or asset unit, or at least one measure associated with a healthcare facility process, or to any other purpose contemplated to implement the method.

Software used to practice the method may also be configured to control the various embodiments of apparatuses such as but not limited to instrumentation apparatuses. Examples of such control uses include but are not limited to transmitting configuration codes to direct a preferred function, alternate function, or optional function of an apparatus; transmitting a code or signal to activate or deactivate an apparatus; transmitting a code or signal to initiate a data transfer; or periodically transmitting a code or signal to invoke or receive the "heartbeat" of an apparatus as previously described herein. Software may also be configured to invoke alternate apparatus functionality when control uses do not yield expected results or responses. Examples of such alternate apparatus functionality include but are not limited to self-corrective functions including apparatus diagnostics or automated remedial actions. Software may also be configured to alert an operator whenever expected functionality is not achieved or automated means of restoring expected functionality are unsuccessful.

Examples of instrumentation apparatuses utilized to implement the method may include but are not limited to at least one RFID scanner advantageously located in proximity to a surgical operating room and utilized before, during and after a surgery. Such RFID scanner may be utilized to detect healthcare facility assets, such as surgical instruments and other assets utilized in a surgery, that are configured to include an RFID-based technology as a durable means of providing identifying information. Uses of such at least one RFID scanner in relation to a surgical operating room or a surgery may include but are not limited to assisting in identifying and counting asset units such as surgical instruments designated for use in a surgery, detecting process uses of an asset unit before, during and after a surgery, determining process timing and movements of asset units, identifying unexpected asset units present in the operating room, detecting expected or unexpected movements of assets or asset units in and out of the operating room, or identifying asset units designated for a non-surgical process step such as but not limited to removal for sterilization, designation for maintenance or obsolescence, or designation for replacement.

Another non-limiting example of instrumentation utilized to implement the method may include but are not limited to at least one RFID scanner advantageously located in proximity to a CSPD room or function. Such RFID scanner may be utilized to detect healthcare facility assets, such as surgical instruments and other assets utilized in a surgery, that are configured to include an RFID-based technology as a durable means of providing identifying information. Uses of such at least one RFID scanner in relation to a CSPD room or function may include but are not limited to assisting in identifying and counting asset units such as surgical instruments designated for use in a CSPD function, where such uses may include but are not limited to cleansing, decontamination or sterilization; or for identifying, locating and counting asset units designated for a surgery, at process steps occurring either before or after the surgery.

Apparatuses utilized in the methods taught herein may also include composites of more than one form of instrumentation apparatus conceived and operably coupled to detect more than one form of durable means of providing identifying information. For example, the RFID scanner apparatuses recited for use in an operating room or a CSPD room or function may be further integrated with one or more other instrumentation apparatuses utilized for qualifying or quantifying a healthcare facility asset or process, and combined to form a single composite instrumentation apparatus. In just one non-limiting example, an RFID scanner may be integrated with a barcode reader into a single composite apparatus, interfaced with a control system such as a computational device, and simultaneously operated for purposes to implement the methods taught herein.

Figure 6A:
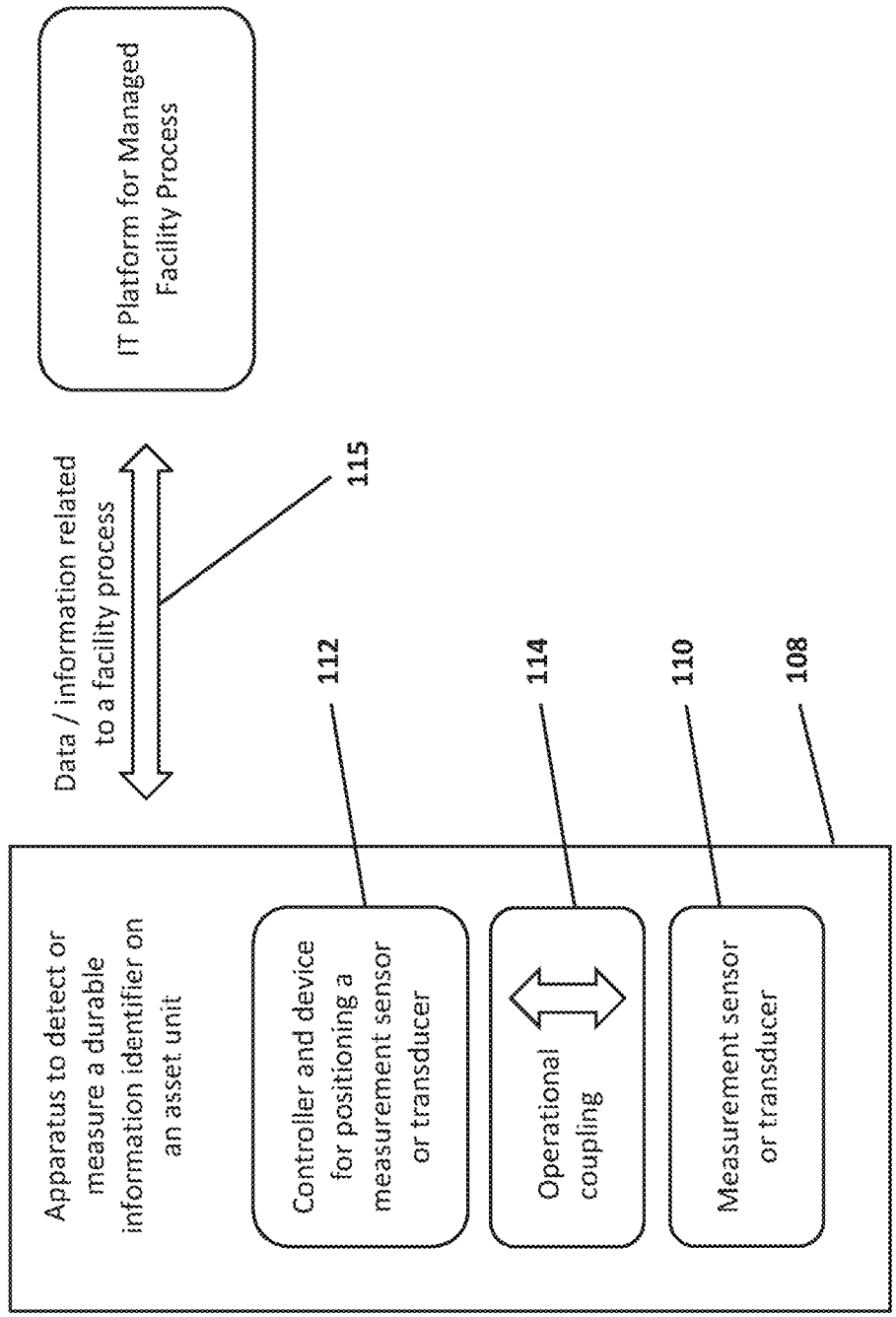
FIG. 6a shows a block diagram of a dynamic scanner apparatus to detect or measure a durable information identifier on an asset unit.

FIG. 6a shows a block diagram of a "dynamic scanner" apparatus for detecting or measuring a durable information identifier on an asset unit, as used to practice the methods taught herein. The dynamic scanner 108 comprises an instrumentation means such as a sensor or transducer 110 for detecting or measuring a durable means for providing identifying information on healthcare facility asset units; further comprises a controller and device for positioning 112 the measurement sensor or transducer 110 in proximity to the asset units or the asset units' means of providing identifying information; and is configured such that the instrumentation means for detecting or measuring further comprises an operational coupling 114 between the sensor or transducer 110 and the controller and device for positioning 112.

An embodiment of a dynamic scanner 108, and related uses thereof, is realized wherein the sensor or transducer 110 comprises an RFID scanner further comprising at least one RFID-sensing antenna or similar form of sensor or transducer, known henceforth as the "RFID sensor", configured to enable the reading of more than one RFID frequency from a grouping of RFID frequencies commonly known and applied in the art. The embodiment is further realized when the RFID sensor is operably coupled 114 to a controller and device for positioning 112 comprising a positioning system. There are many such positioning systems commonly known in the art including but not limited to what is known as a linear motion table, also known as an XY, XYZ or a gantry table. Although the embodiment taught herein utilizes a linear motion positioning system, the apparatus is also readily implemented using any form of nonlinear motion device or positioning system. An alternate embodiment may include a compound positioning system such that during operation the RFID sensor undergoes translational motion along a path such as but not limited to a linear path, while simultaneously undergoing an independent compound motion such as but not limited to a rotational motion, an orbital motion, a quasi-rotational or quasi-orbital motion, a transverse linear motion or a random motion.

The controller and device for positioning 112 is further realized when the positioning system is interfaced to a computational means that may comprise processors and memory, and is configured to move during operation in at least one controllable or repeatable pattern of motion when used for the purposes of achieving the methods taught herein. In a preferred embodiment, the controller and device for positioning 112 is configured to drive the location of the positioning system and simultaneously determine the location of a sensor or transducer such as an RFID sensor in a 2-D or 3-D space. In a further preferred embodiment, the dynamic scanner 108 is further interfaced to an IT platform 115 configured and utilized for managing healthcare facility assets and processes.

Further to the embodiment, the positioning system is conceived to move the sensor or transducer such as an RFID sensor in operable proximity to any point coinciding with or correlated to a detection surface on which the asset units may be placed. Such placement and pathways of motion are conceived to improve the dynamic scanner's 108 ability to detect or reliably measure at least one aspect of the asset units as may be oriented to or placed on the detection surface. Further to the embodiment, through the combined means for detecting or measuring at least one aspect of the asset units and means for determining the location of the positioning system, a means is provided by which the location of at least one of the asset units positioned on a detection surface may be determined. Such means may utilize computational methods such as but not limited to triangulation or signal strength analysis to further refine the accuracy of the determined location of the at least one asset.

Figure 6B:
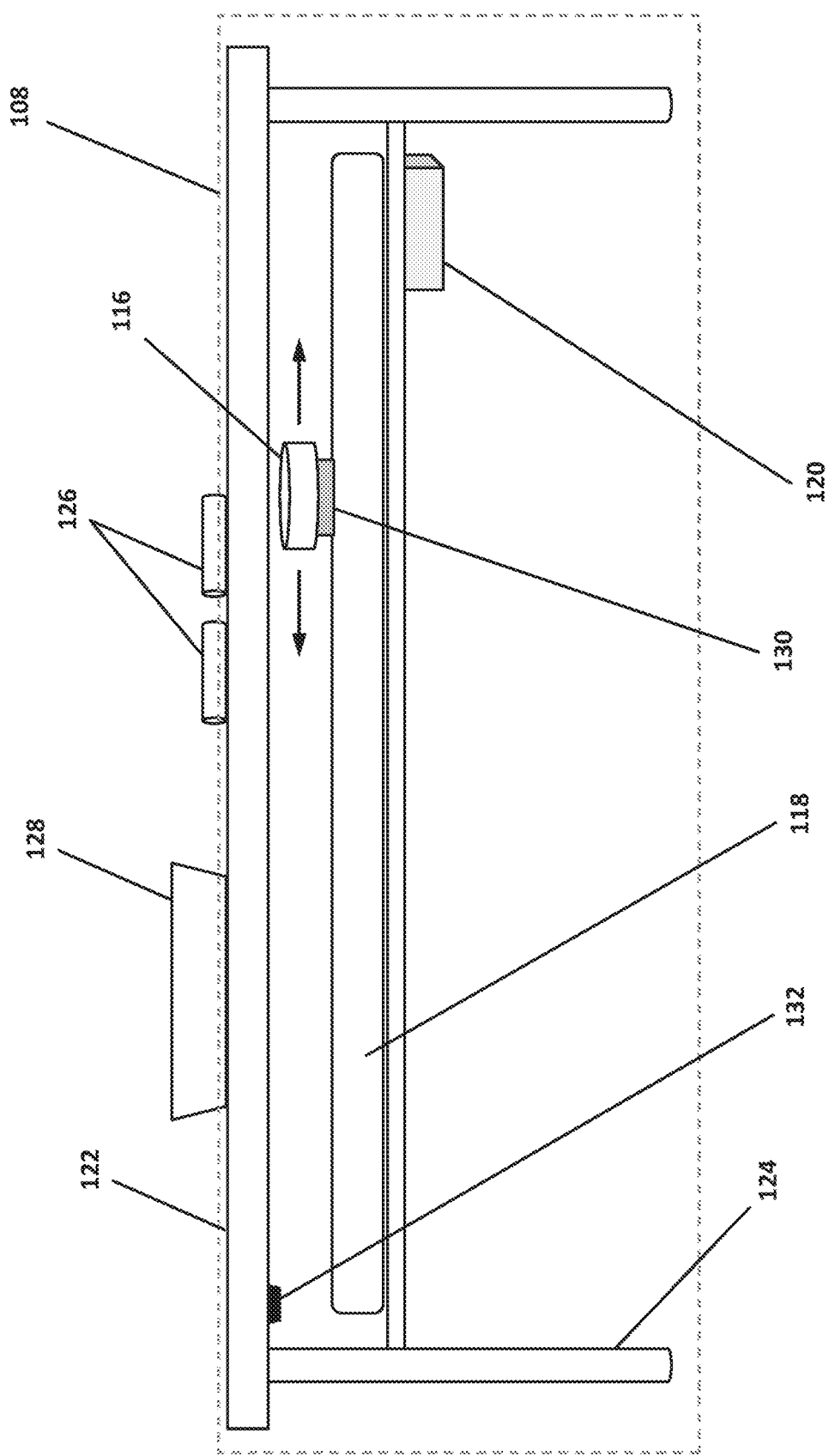
FIG. 6b shows a preferred embodiment of a dynamic scanner apparatus.

FIG. 6b shows a preferred embodiment of a dynamic scanner 108 apparatus, wherein at least one RFID sensor 116 is controllably positioned by a positioning system such as but not limited to a linear motion table 118 interfaced to a control system such as a computational means 120. The at least one RFID sensor 116 and the linear motion table 118 are preferably mounted on or near the underside of a detection surface 122 comprising a generally horizontal plane and preferably part of a structural fixture 124 configured for utilization in a healthcare facility. In operation, the asset units 126 are placed on the top of the detection surface 122. Alternately, containers 128 of the asset units 126 such as but not limited to trays of the asset units may be placed on the detection surface 122. Following the placement of the asset units 126 or containers 128 of the asset units 126 on the surface, the dynamic scanner 108 may be initiated and utilized to detect or measure the asset units 126 at any time preferable or advantageous to implementing a method as taught herein. Initiation may be done via control code transmitted by the control system, or may be done via a manual initiation step utilized by an operator. Just one non-limiting example of a manual initiation step comprises a switching operation. Initiation by a control system may also or alternately occur after determining a need to detect or measure assets as directed by a software application practically applied to implement the apparatus. Such software directed initiation may come as a result of an operator initiated step, a software determined and in initiated step, or automatically as a result of any means of sensing the presence of the asset units 126 further integrated to the preferred embodiment of the apparatus, such as but not limited to an optical sensing means, a proximity sensing means, a force sensing means or a simple switching means. Once initiated, the linear motion table 118 may be operated to move the RFID sensor 116, preferably over at least a portion of the area comprising the underside of the detection surface 122, and more preferably over the entire area of the underside of the detection surface 122. Such motion may include a multiplicity of any combination of linear or non-linear motions as needed to move the RFID sensor 116 through the at least portion of the aforementioned area. Such motion may also cause the RFID sensor 116 to pass over the same portions of the area more than once. The preferred embodiment is further realized when the RFID sensor 116 is operated during the process of moving the linear motion table 118, such that the asset units 126 placed on the detection surface 122 are detected and measured by the apparatus. The preferred embodiment further provides for means to transmit information associated with the detection and measuring process from the apparatus to an IT platform configured and utilized for managing healthcare facility assets and processes. Such transmitted information may include but is not limited to information associated with a durable means of identifying information utilized on the asset units, or information associated with the location of the asset units. The preferred embodiment further provides for means to stop the detection and measuring process, such as but not limited to a manual stop step or a software determined and transmitted control code.

A further embodiment is conceived in which a multiplicity of RFID sensors 116 is provided integral to the apparatus, such as any number of RFID sensors 116 that are configured to be optimized to detect or measure preferential frequencies. In this embodiment, a positioning system such as but not limited to a linear motion table 118 may be used to move a docking means to selectively couple or decouple any of the RFID sensors 116. Such coupling may include a physical coupling 130 of an RFID sensor 116 such that further motion of the linear motion table 118 causes motion of the RFID sensor 116 for positioning purposes described herein, and may also include a means of operably coupling such as but not limited to electrical or optical coupling of the RFID sensor for detection and measuring purposes described herein. In operation, the apparatus may be controlled to advantageously change couplings to the various RFID sensors so that different RFID frequencies may be measured.

A further embodiment utilizes an RFID chip 132 fixed to a preferentially selected location on or in proximity to the apparatus, such that an RFID sensor 116 coupled to a positioning system may be moved to the fixed RFID chip 132 at any time as directed by a control system, and the RFID sensor 116 utilized to detect or measure the fixed RFID chip 132. In one non-limiting example of this embodiment's use, a control code may be transmitted to the embodiment as a result of an IT platform's function to detect the heartbeat of the apparatus. Such control code may instruct the apparatus embodiment to position the RFID sensor 116 near the fixed RFID chip 132 and read the information stored on the RFID chip. Such information may be processed to determine that the apparatus is functioning correctly, triggering a corresponding at least one datum of information to be transmitted back to the IT platform. Such information may also be processed to determine that the apparatus is not functioning correctly, triggering a corresponding at least one additional datum of information to be transmitted back to the IT platform. In this case, such information transmitted back to the IT platform may also include information that identifies at least one characteristic of the failure, such as but not limited to a cause of the failure or process step where the failure occurred.

Alternate embodiments of preferred functionality of the apparatus as described may be accomplished with any means of sensing durable information. The use of RFID as recited is not meant to be limiting.

Figure 7:
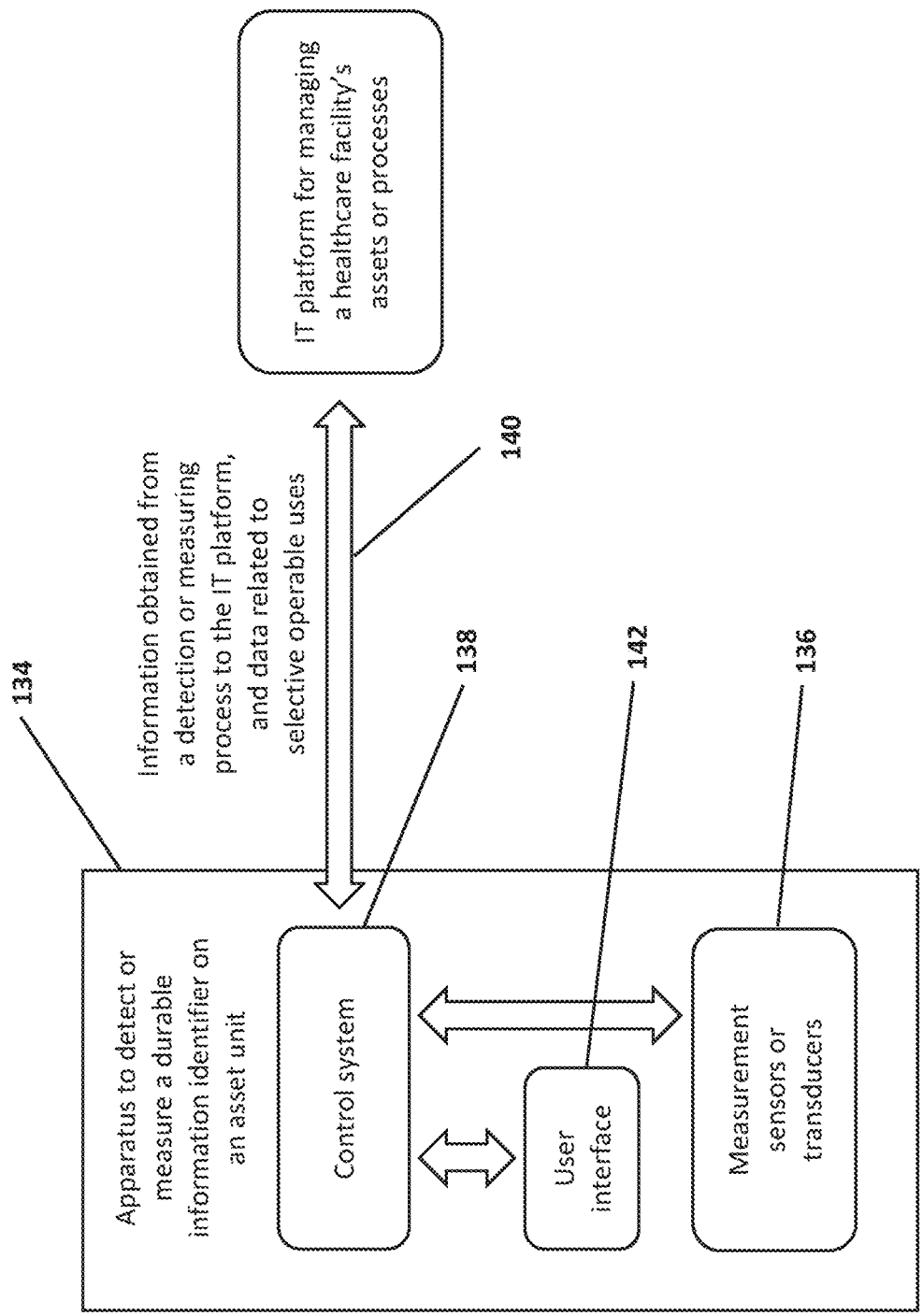
FIG. 7 shows a block diagram of an interactive scanner apparatus to detect or measure a durable information identifier on an asset unit.

FIG. 7 shows a block diagram of an "interactive scanner" apparatus to detect or measure a durable information identifier on an asset unit, as used to practice the methods taught herein. The interactive scanner 134 comprises an instrumentation means such as any number of sensors or transducers 136 for detecting or measuring a durable means for providing identifying information on healthcare facility asset units; further comprises a control system 138 with means for communication and processing of data utilized in an IT platform further configured and utilized for managing healthcare facility assets and processes; is operably interfaced 140 to such IT platform; is configured to transmit information obtained from at least one detection or measuring process to such IT platform; is configured to receive, process and provide for selective operable uses based on at least one datum received from such IT platform; and further comprises at least one user interface 142.

An embodiment of an interactive scanner 134 and related uses thereof comprises any means as taught herein for detecting or measuring information associated with the asset units. Such means may preferably include but is not limited to at least one RFID chip. Such means may also include any combination of means for detecting or measuring information. Just one non-limiting example of such combination, sensors and transducers 136 in an interactive scanner 134 comprise an RFID sensor and a barcode reader, both utilized in the same apparatus. The embodiment may include any control system 138 with means of data communication commonly known in the art, particularly for the purposes of transmitting or receiving at least one datum while the embodiment is operably interfaced 140 to an IT platform. A preferred embodiment may utilize wireless communication means for such data communication purposes. The control system 138 embodiment may include any means of data processing commonly known in the art. Such control system 138 means may include but are not limited to the integration of at least one microprocessor, microcontroller or similar computational means that may comprise processors and memory, any of which may utilize software or firmware practically applied to achieve the functionality of the interactive scanner 134, and also to provide operation and control of a user interface 142. Such user interface 142 may include but is not limited to an interactive display. Such user interface 142 may also provide an operator means for selecting various operable uses of an interactive scanner 134 and receiving information related to such operable uses.

In one embodiment of the apparatus, a dynamic scanner 108 and an interactive scanner 134 are integrated and operated as a single instrumentation apparatus. Although an interactive scanner 134 may be embodied as either a fixed or mobile apparatus, one preferred embodiment comprises an RFID sensor in a handheld detection or measuring apparatus. Further to the preferred embodiment, the RFID sensor is operably coupled to a control system 138, and the control system 138 is operatively interfaced 140 to an IT platform for managing healthcare facility assets and processes. Further to the preferred embodiment, the control system 138 is enabled to transmit or receive data either to or from the IT platform, and the control system 138 is configured to operate the interactive scanner 134 in accordance with such data.

Figure 8:
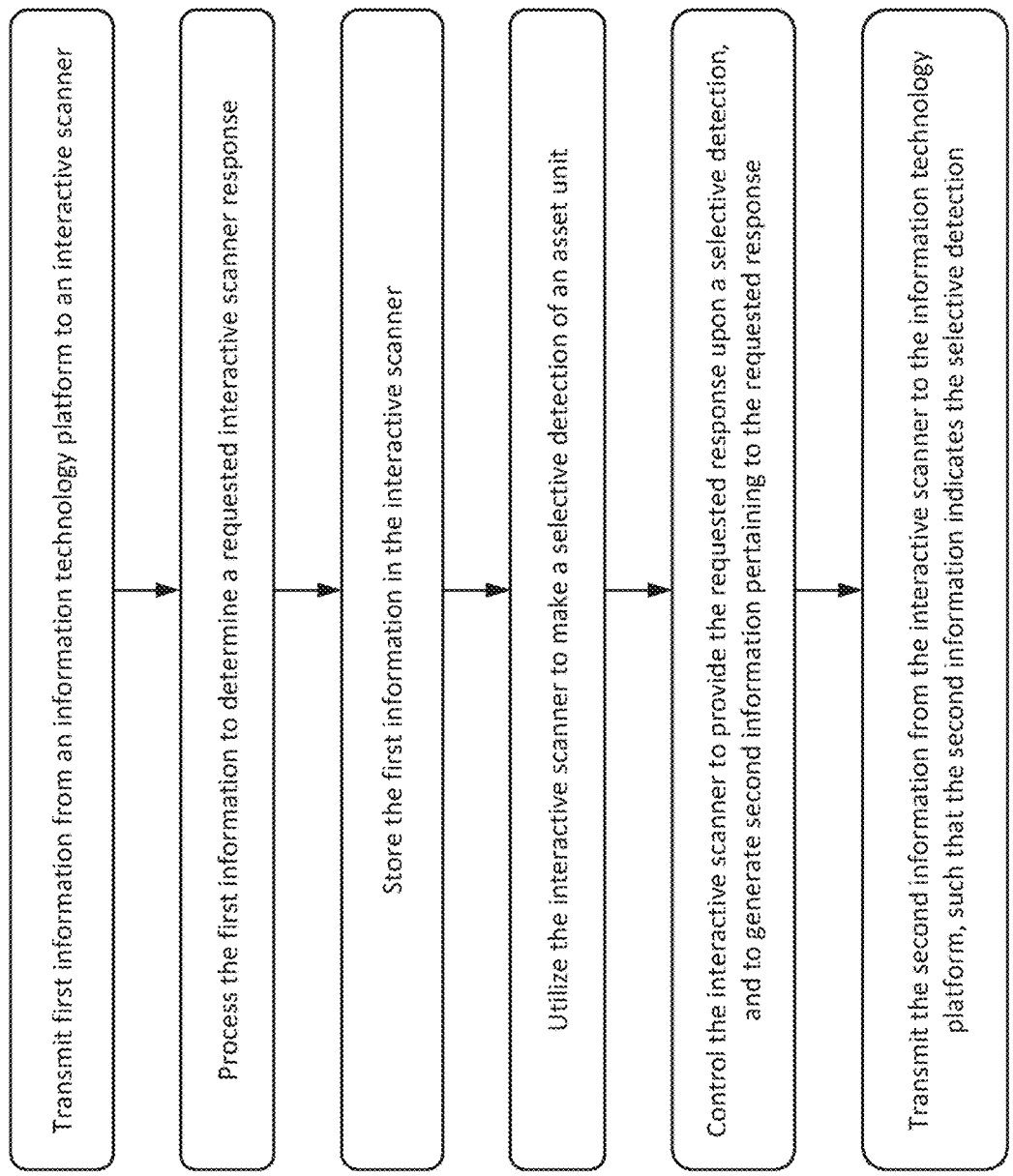
FIG. 8 shows a block diagram of method steps for the selective detection of asset units for use in a healthcare facility process.

FIG. 8 shows a block diagram of method steps for the selective detection of asset units for use in a healthcare facility process. In one non-limiting example of the practical application of an interactive scanner 134 as taught herein, an IT platform may transmit information to or from the interactive scanner 134 such as but not limited to information about an asset or an asset unit. Such information may include an asset name, asset class or unique identifier associated with at least one asset unit as stored in at least one database associated with the IT platform, such as but not limited to an HFIL. Such transmission of information from an IT platform may be carried out in response to a request for the information transmitted from the interactive scanner 134, and such request may be initiated by an operator through a user interface. In just one non-limiting example, an operator may utilize a user interface on an interactive scanner 134 to request all unique identifiers of all asset units of a particular asset existing in usable inventory at a healthcare facility. Such request may be transmitted from the interactive scanner 134 to an IT platform that includes at least one database that contains such unique identifier information. In response, the IT platform may transmit the requested data to the interactive scanner 134. The data transmitted from the IT platform to the interactive scanner 134 may then be processed, stored or utilized by the interactive scanner 134 in a number of ways advantageous to the apparatus.

In a non-limiting example, the interactive scanner 134 may be controlled to only respond to detections or measurements of asset unit unique identifiers that are included in the data transmitted from the IT platform as described, and to ignore other detected or measured unique identifiers. Accordingly, the interactive scanner 134 may hence be utilized as a selective detector of a preferred subset of the asset units, which may be particularly useful for locating asset units of such subset when such asset units are integrated among other non-preferred asset units. Such use as a selective detector may also benefit an operator that is unfamiliar with a particular asset, such that the interactive scanner 134 may be used to find example units of assets unfamiliar to the operator. Further to such use, data transmitted from an IT platform may include an image of an asset utilized to provide further assistance to an operator. Further still, any apparatus as taught herein may also include means for acquiring an image, such as through a camera, such that an acquired image may be utilized in implementing any of the methods taught herein.

Such interactive scanner 134 use may also arise from the transmission of data from an IT platform without the preliminary step of being requested by the interactive scanner 134. In a non-limiting example, the interactive scanner 134 may receive information transmitted from an IT platform in which the information may comprise a unique identifier of at least one missing asset unit. Accordingly, the interactive scanner 134 may be utilized as a selective detector of the at least one missing asset unit. Such utilization may be particularly useful in assuring that a missing asset unit such as but not limited to a surgical instrument or similar surgical asset has not been left inside of a patient undergoing a surgical procedure.

In yet another series of non-limiting examples, an interactive scanner 134 may be used in CSPD functions related to identifying and retrieving assets for use in a healthcare facility function such as but not limited to a surgery. For example, an interactive scanner 134 may receive a grouping of unique identifiers data from an IT platform, with said unique identifiers known to belong to a plurality of the asset units sought for use in a healthcare facility function. The interactive scanner 134 may hence be used to detect or measure unique identifiers from a body of asset units stored in a CSPD-related location, such as but not limited to usable inventory, and the interactive scanner 134 may be configured to provide an indicator only when any one or more of the sought unique identifiers are detected. Upon such detection, at least one such asset unit associated with the detected unique identifier may hence be removed from inventory and included for use in the healthcare facility function, and the interactive scanner 134 may be configured to store the unique identifier of the removed at least one asset unit and subsequently process such unique identifiers including but not limited to transmitting the unique identifiers to an IT platform. Upon such removal the interactive scanner 134 may also be configured to stop providing further indications of detecting other instances of the removed asset unit. Such use in the functional mode of this example is to assist an operator seeking to find instruments for the common surgery-related purpose of removing one or more asset units from usable inventory and creating what is commonly known in the art as a surgical tray. In another example use in this mode of function, the interactive scanner 134 may also be configured to reject any asset unit that is detected or measured for possible inclusion in a grouping such as but not limited to inclusion in a surgical tray, with rejection occurring particularly for the purpose of assuring the grouping does not include asset units that are not appropriate for or intended to be included in the grouping. Such rejection functionality may be overridden by an operator if deemed advantageous to the healthcare facility function.

In yet another non-limiting example, pertinent to an interactive scanner 134 or any other like instrumentation apparatus for detecting or measuring taught herein, an interactive scanner 134 may be used in conjunction with a control code such as a command from software or firmware to "mark" an asset unit for any variety of treatments associated with the asset unit, such as but not limited to "marking" an asset unit for cleansing, decontamination, sterilization, maintenance or obsolescence. The process of marking may include but is not limited to steps including making a detection or measurement of the unique identifier of an asset unit to be marked, and then indicating in software, preferably via a user interface, that the unique identifier of the asset unit to be marked is designated as such. When marked, the unique identifier of the asset unit may preferably be designated for treatment in a database such as but not limited to an HFIL, and therefore no longer be included in the subset of assets designated as usable inventory. The designation for treatment in a database may also include information identifying the treatment form. In utilization for any of the methods taught herein, an interactive scanner 134 or any other like instrumentation for detecting or measuring taught herein may be further configured to provide an indication if a scanned object has been marked for a treatment. The utility of such function includes but is not limited to preventing asset units marked for treatment from being included in a grouping such as a surgical tray, or for detecting when such asset units have been inadvertently included in such grouping.

Another non-limiting example of use is provided in which an interactive scanner 134, as configured to transmit or receive data, is part of a healthcare facility process tracking system involving at least one additional instrumentation apparatus for detecting or measuring at least one healthcare facility asset. In this example of use, the interactive scanner 134 detects unique identifiers of asset units such as but not limited to surgical instruments being pulled from a first location, such as but not limited to a storage location, and transferred to at least one second location. Such use is commonly done in CSPD functions as part of the creation of a surgical tray. Further to this example of use, one or more asset units may be scanned by an interactive scanner 134 at the first location. In addition to the asset unit's unique identifier, data determined by or collected by the interactive scanner 134 may also include process data such as the date and time of the scanning, the identification of the operator performing the scanning and the location of the scanning. Further to the use, the interactive scanner 134 may be configured to transmit the aforementioned data collected by the interactive scanner 134 to the at least one additional instrumentation apparatus. Such additional instrumentation apparatus may include but is not limited to another means of detecting or measuring the same form of unique identifier as detected by the interactive scanner 134. A preferred embodiment of an additional instrumentation apparatus may include a dynamic scanner I 08 being used to detect or measure asset units being placed in a surgical tray. When the asset units are subsequently detected or measured by the additional instrumentation apparatus, the combination of data arising from detections or measurements at both a first location and a second location may be utilized to provide process data and accomplish methods of process management as taught herein. Examples of such uses include but are not limited to determining dates and times related to the process steps, and assuring that the unique identifiers of all asset units detected or measured as received at a second location match the unique identifiers of all asset units first detected or measured at the corresponding first location.

In yet another use contemplated for an interactive scanner 134, process data may be utilized to determine optimal sequences of asset unit use. Such optimal sequences may include but are not limited to the sequence in which assets are removed from inventory and used to create a surgical tray. In use as taught herein, an IT platform may transmit to an interactive scanner 134 the entire list of asset units to be included in a surgical tray, and may also transmit the sequence for which the asset units can be removed from inventory in a manner that minimizes process time or minimizes the probability of process errors.

In yet another embodiment of an apparatus, an instrumentation apparatus such as an interactive scanner 134 as taught herein may be implemented as an integral aspect of a container or storage vessel. In just one non-limiting example, such apparatus may be embodied as a container carried by an operator or positioned by any automated positioning means and utilized for purposes such as retrieving asset units for purposes including but not limited to creating a surgical tray. The functionality of the interactive scanner 134 may be consistent with those functions taught herein, and the container may be implemented as a ready means of transporting a grouping of asset units, whether manually or via an automated means, from a first location to a second location. In another use, a storage vessel configured to include a means of detecting or measuring information associated with healthcare facility assets, such as but not limited to an interactive scanner 134, may be further configured to provide information to an IT platform whenever an asset unit is removed from the storage vessel. Such removal information may be utilized in any number of the healthcare facility asset and process management methods taught herein. A collection of such storage vessels may be used to implement an inventory storage system featuring integrally operated apparatuses for detecting or measuring a durable mean of identifying information.

Figure 9:
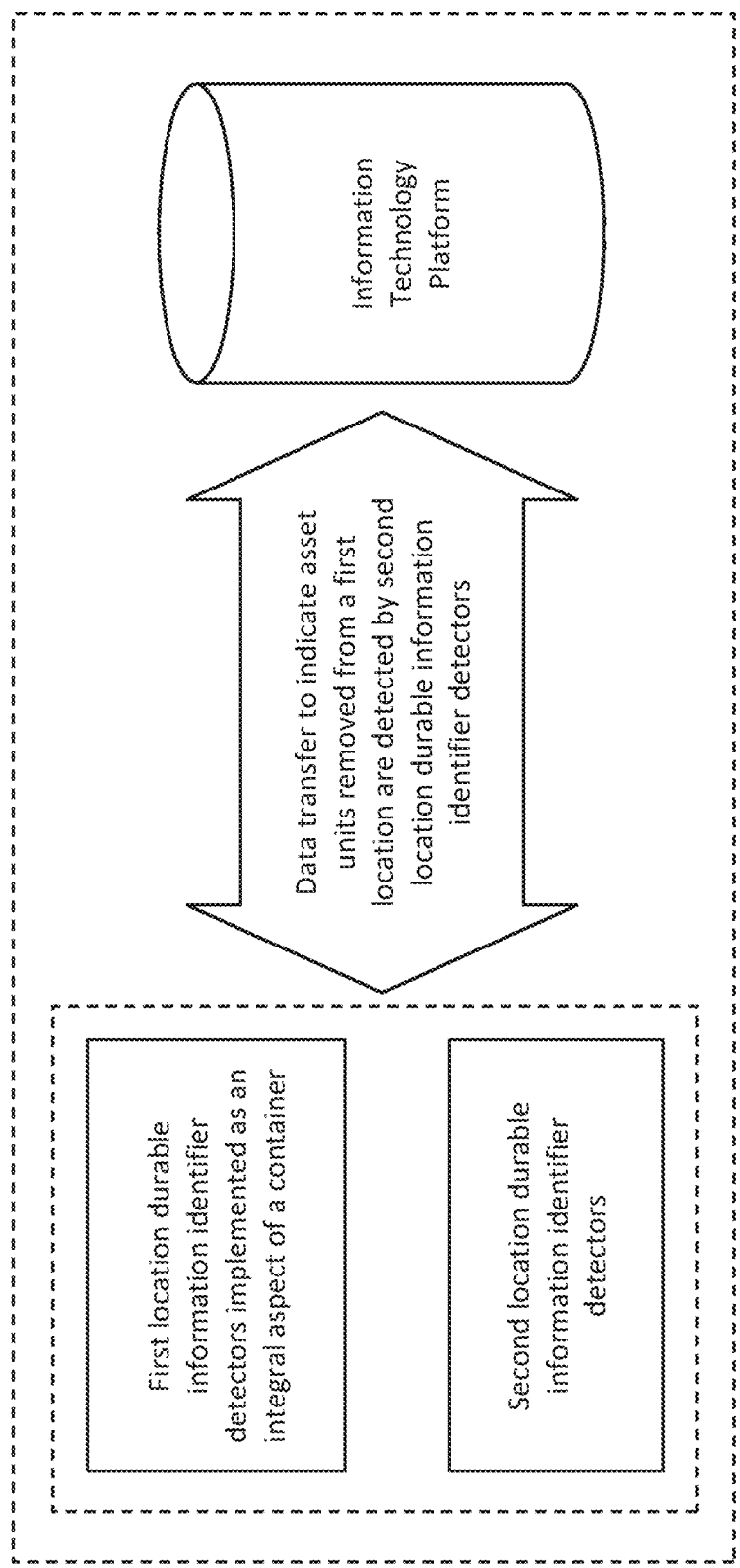
FIG. 9 shows a block diagram of a system for process management in a healthcare facility.

FIG. 9 shows a block diagram of a system for process management in a healthcare facility, in which asset unit removal information is further used in a process management system to assure that whenever an asset unit is detected as being removed from a first operation or a first location then it is tracked to assure that the asset unit is eventually detected at a second operation or a second location, and the information is further configured to cause a process management response in cases where such second detection does not take place within an expected timeframe or occurs in any other unexpected manner. Such use may further enable alternate or responsive processes contemplated to remedy the lack of expected detection or unexpected detection.

In another non-limiting example of use, an unexpected event or finding associated with an asset being removed from usable inventory may occur. Examples of such unexpected events for findings may include but are not limited to an asset unit being dropped or damaged. If such unexpected event occurs, an interactive scanner 134 may be used to mark the asset unit and designate the asset unit for a particular treatment. The process control system may then be further configured to prevent the asset unit from being returned to usable inventory until the treatment has been completed, and to transmit control codes or unique identifiers to at least one instrumentation apparatus for detecting or measuring a unique identifier at a second location associated with the treatment process. In doing so, such transmitted control codes or unique identifiers may be used to assure that the treatment process takes place on the asset before it may be returned to usable inventory and utilized in a healthcare facility process.

In yet another embodiment of an apparatus as taught herein, including but not limited to a dynamic scanner 108 or an interactive scanner 134, an apparatus may be further configured to listen for audible signals such as but not limited to voice commands provided by human operators. Such voice commands may be used for a plurality of purposes or functional uses such as but not limited to those examples disclosed herein. Just one non-limiting example of use includes receipt of a voice command that activates an algorithm in software practically applied to implement any of the methods taught herein. Such algorithms may include functions to identify, locate or mark an asset unit.

Additional software algorithms are conceived in which process and asset use data are used in machine learning or artificial intelligence routines to further optimize processes or assure process compliance. In just one non-limiting example, a software algorithm may provide for the most likely sequence of asset unit uses in a process. An example of such might be the sequence in which assets or asset units such as but not limited to surgical instruments are used in a surgical procedure. Any of the apparatuses as taught herein may be used to detect utilization of an asset or asset unit, subsequently "predict" the next asset or asset unit to be used in the process, and subsequently identify the location of the predicted next asset or asset unit to an operator. Such may be used to improve process timing or efficiency.

These and numerous other uses are readily achieved using an interactive scanner 134 configured with functionality such as that recited herein. The examples given are therefore not limiting, nor are they limited to RFID sensors or limited to any particular class of assets. Each apparatus taught herein may also be configured to reject or prevent uses of asset units that are not included in usable inventory. Each apparatus use, whether recited or not, may include the use of software practically applied to implement the intended use of the apparatus. Additional information and data associated with any of the apparatuses taught herein may include but is not limited to a unique identification of the apparatus and the location of the apparatus in a healthcare facility.

Numerous aspects of the methods and apparatuses for managing healthcare assets may be realized or may benefit from uses of software practically applied to facilitate implementation and use of the methods and apparatuses. Such software is conceived to be implemented in functional applications configured for use at physical process points related to the methods, such process points including but not limited to a healthcare facility, a manufacturer, a vendor or supplier, or a healthcare professional's office. Such software is also conceived to be implemented in association with non-physical process points, such as but not limited to applications that facilitate a coordination process between a healthcare facility and a manufacturer, or a healthcare facility and a vendor. Such software applications may include user interfaces to facilitate functional inputs and outputs from and to at least one human operator or user, may be implemented as an IT platform-resident application or a remote application accessed through means such as a network or internet connection, and may be implemented as a mobile application. Such applications may function independently, or may be operably linked to databases common to the methods such as but not limited to an MAL, a UPD or an HFIL. Such applications may be further operably linked to healthcare facility EMR systems or internal data systems. Software may be implemented by any means of coding known and commonly applied in the art.

A software application in a healthcare facility may be configured to include modules dedicated to particular healthcare facility functions. Examples of such functional modules include but are not limited to a module dedicated to operating room processes, a module dedicated to CSPD processes, a module dedicated to the management of inventory and supply chain and a module dedicated to administrative processes.

Figure 10A:
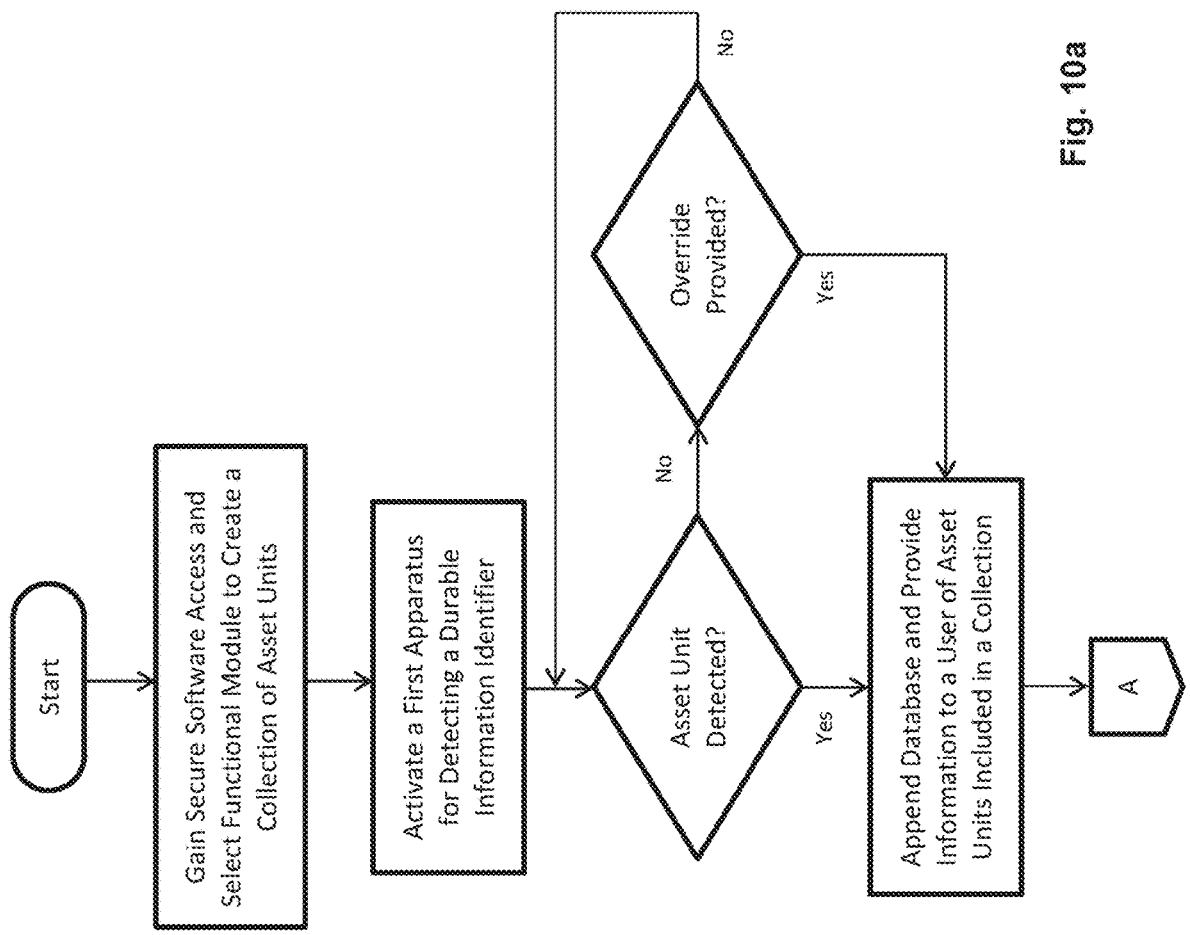
FIGS. 10a-10c show flowcharts of software practically applied to create a collection of asset units.
Figure 10B:
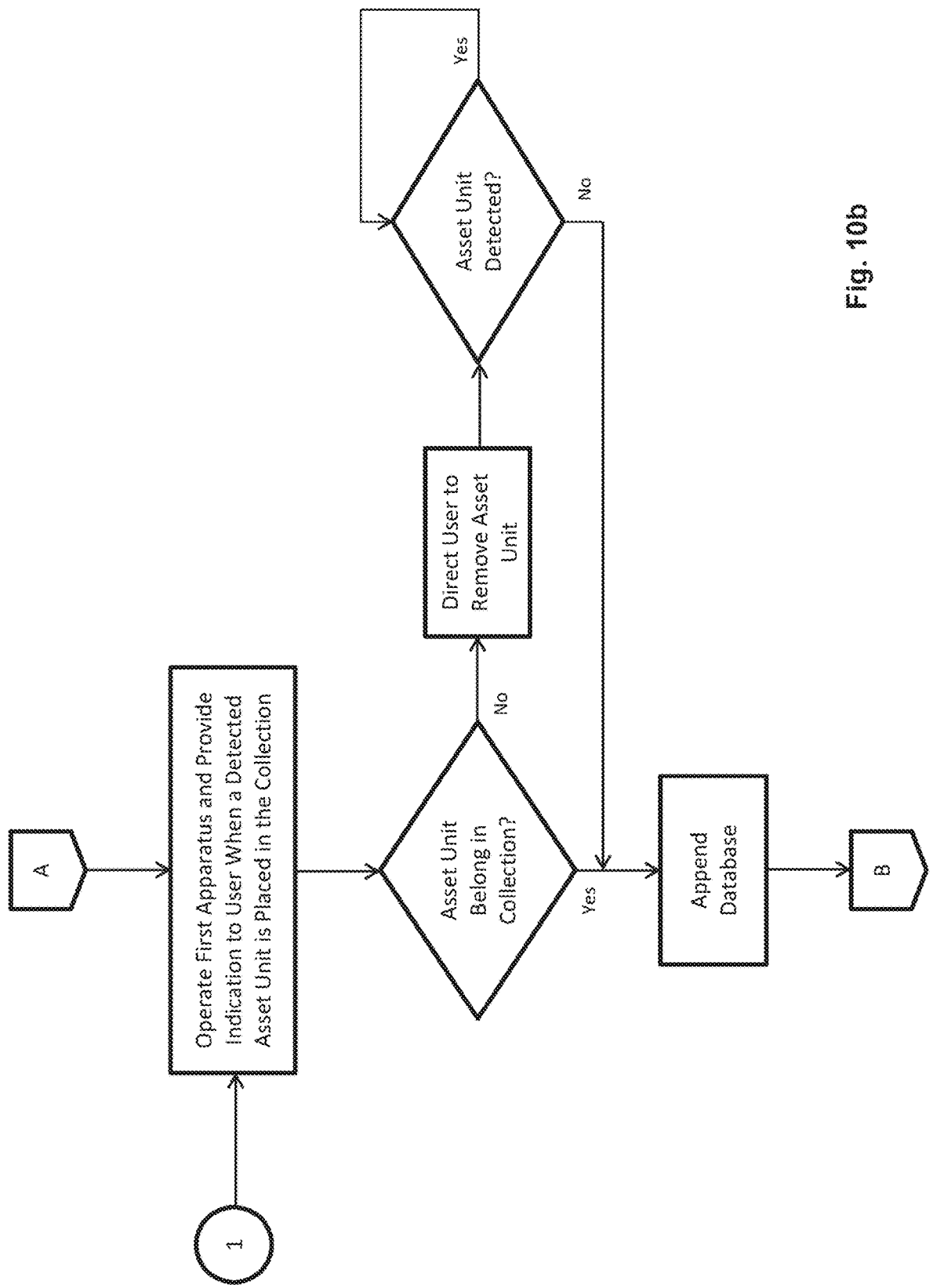
Figure 10C:
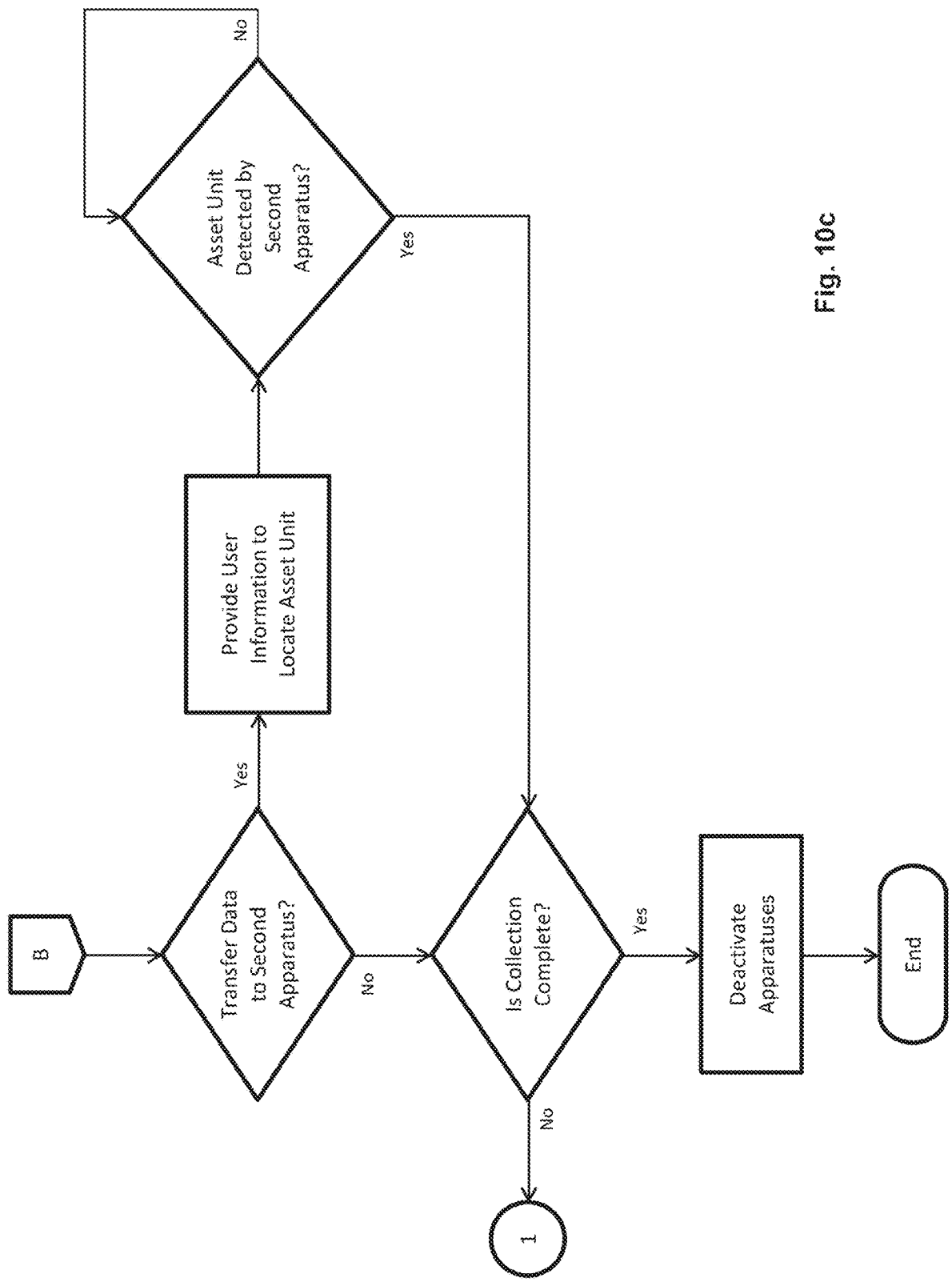
Figure 11B:
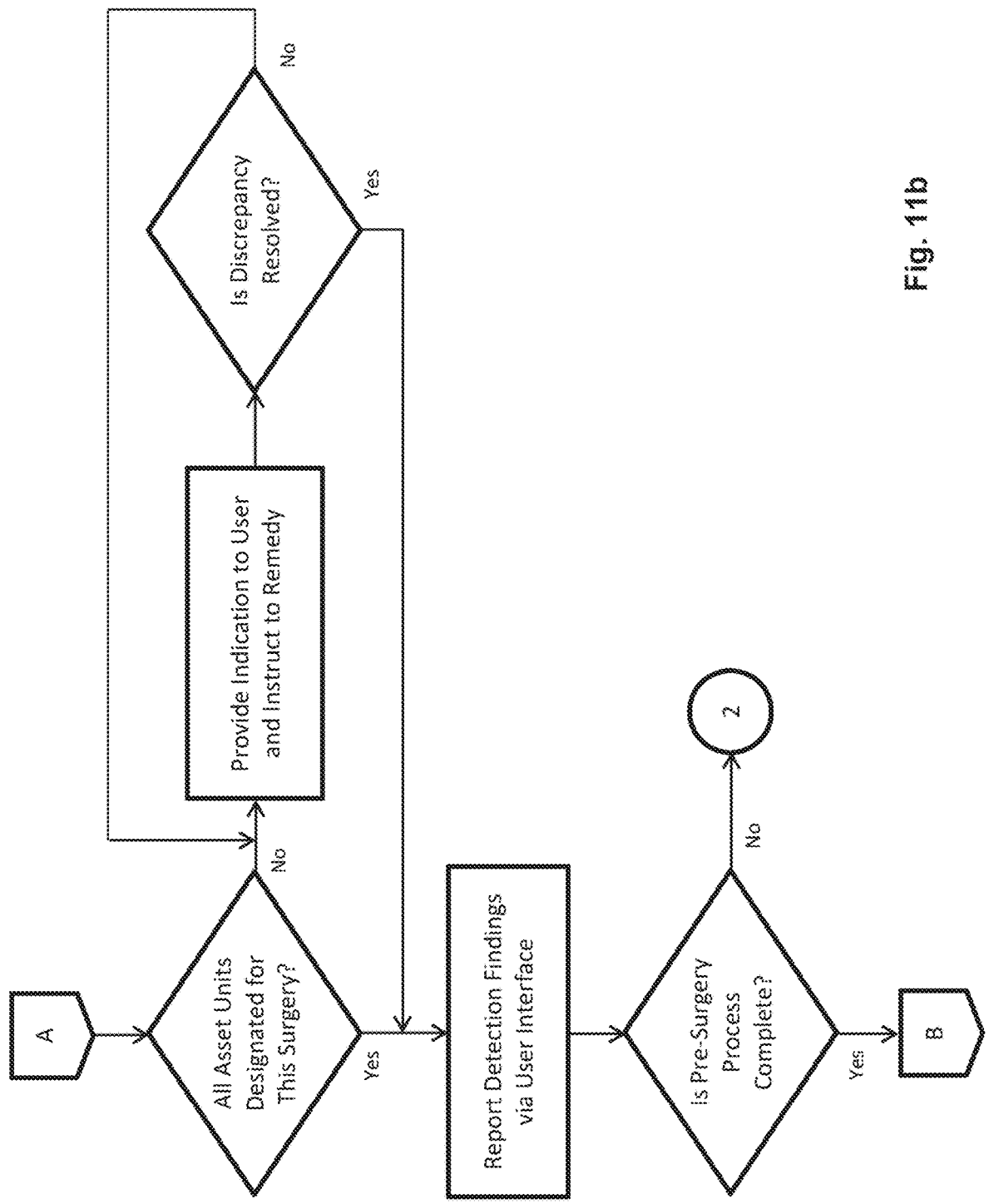
Figure 11C:
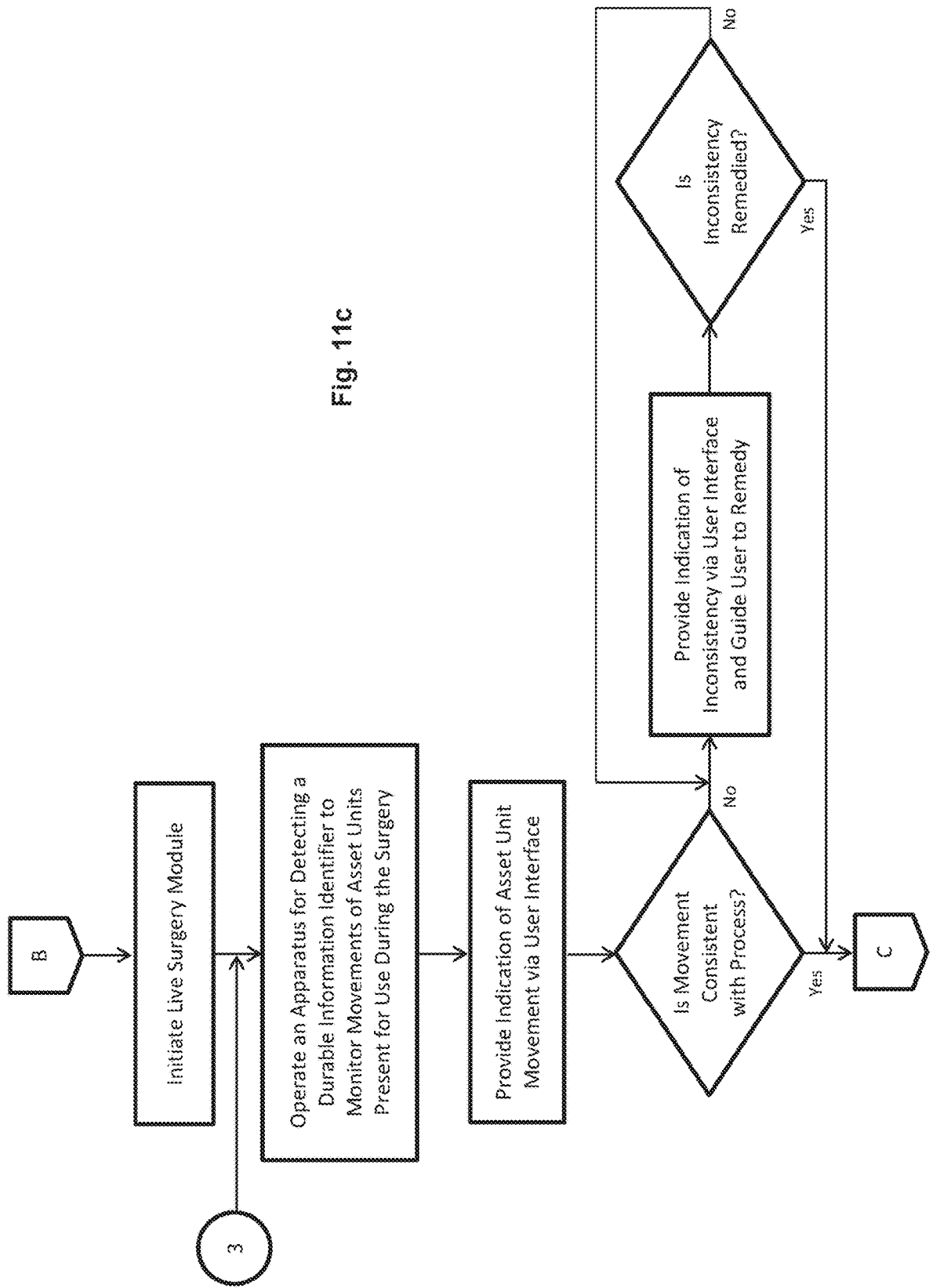
Figure 11D:
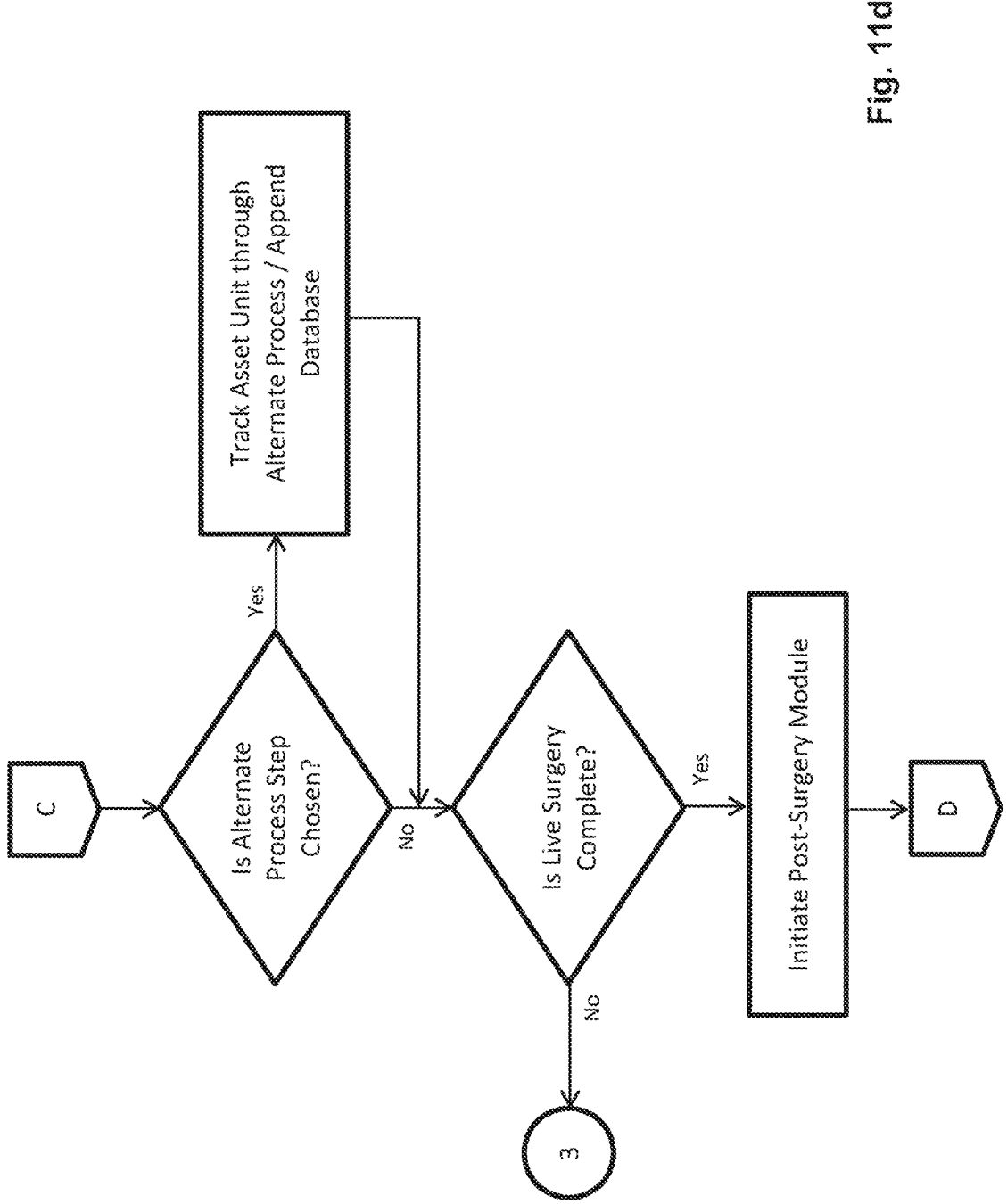
Figure 11E:
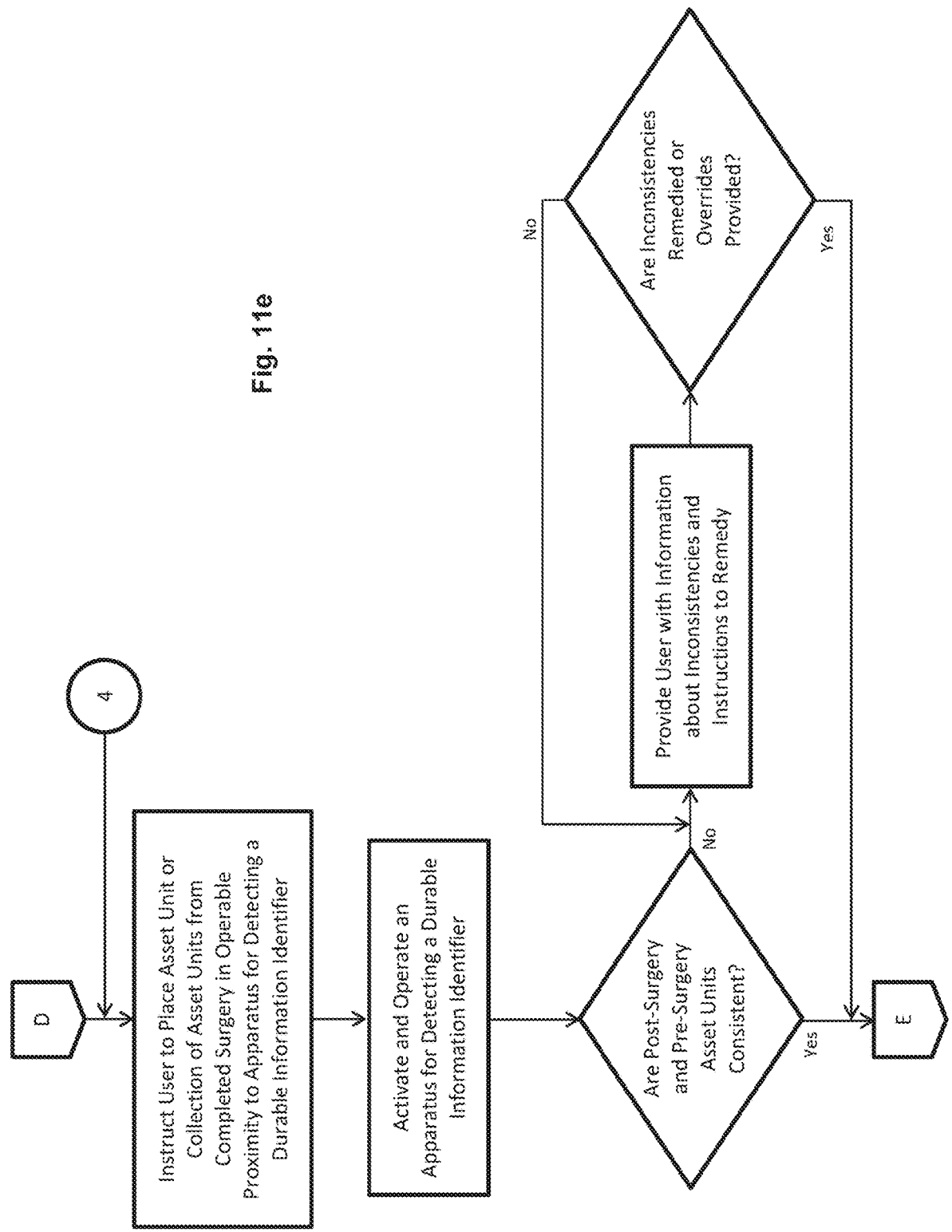

With reference to FIGS. 10a-10c, a functional module dedicated to CSPD functions may include but is not limited to the following practically applied software steps and routines (i.e. a "CSPD routine"):

A software routine such as a CSPD routine that permits an authorized user at a healthcare facility to gain secure access to subsequent software functions.

A software routine such as a CSPD routine that allows an authorized user to select and gain access to the functional module dedicated to CSPD processes.

A software routine such as a CSPD routine that allows an authorized user to select and differentially gain access to specific CSPD processes such as but not limited to asset cleansing, decontamination or sterilization; creating at least one collection of assets or asset units such as but not limited to creating a surgical tray; or releasing the at least one collection to a healthcare facility function outside of the CSPD. Such routine may also be configured to provide the user with instructions or specifications related to completing a process. For example, a routine may provide instructions for creating at least one collection of assets preferred in completing a process step. In a non-limiting example, such collection may be at least one surgical tray containing surgical instruments for a surgery, such specifications may include a list of surgical instruments to be included in each of the at least one surgical tray, such list being derived from information stored in at least one database, and such instructions may include directions to complete related process steps or prepare for next process steps.

A software routine such as a CSPD routine that allows an authorized user to make selections of assets, asset units or collections of assets for subsequent use in a healthcare facility function. Such routine may include steps of placing such collection of assets in an object for containing the collection, such as but not limited to a surgical tray. In a non-limiting example of one such routine, a user may be permitted to select a type of surgical tray to be created. Such selection of a surgical tray may be categorized by types of surgical trays such as but not limited to standard trays comprising surgical asset units common to surgical procedures, or to surgical trays comprising surgical asset units specific to an individual surgery. Examples of the latter include surgical trays comprising surgical asset units specifically chosen for a unique patient's surgery or for meeting the preference of a specific healthcare professional such as a surgeon.

A software routine such as a CSPD routine that allows an authorized user to selectively choose to receive software use guidance or help at any point during the operation of the software.

A software routine such as a CSPD routine that provides an authorized user with ancillary information about any selection made. An example of such includes but it not limited to information about a surgery for which at least one surgical tray is being completed. Such information may include but is not limited to the name of the patient, identifying characteristics of the patient, healthcare process information related to the patient, the name of the surgeon, the type of surgical procedure to be performed, the date and time of the surgical procedure to be performed, and any collection of or summary of information about the assets required for the surgical procedure.

A software routine such as a CSPD routine that directs an authorized user to follow healthcare facility process steps required for the process to be completed. For example, if a surgical tray is to be created then the software routine may direct the user to complete a series of process steps, beginning with a first process step, and may give instructions for correctly completing such process steps.

A software routine such as a CSPD routine that causes at least one apparatus associated with a process step to be activated or deactivated in accordance with a method or process step. In a non-limiting example during a process step in which a user is directed to place at least one of the assets such as an empty surgical tray in operable proximity to an apparatus for detecting or measuring at least one healthcare facility asset, the software routine may send a control code to such apparatus thus enabling it to detect whether or not the process step has been completed. Examples of such apparatuses may include a dynamic scanner I 08, an interactive scanner 134 or any other instrumentation apparatus as taught herein. The routine may further be configured such that subsequent routines cannot be initiated until such process steps are completed as indicated by the apparatus or until an optional user override is provided. The routine may further be configured such that the durable means of identifying information measured from the at least one asset is appended to a database and stored.

A software routine such as a software routine such as a CSPD routine that provides an indication to a user, such as through a user interface, that an apparatus has been activated, is in use, is making progress toward performing a function, or has completed its function either successfully or unsuccessfully.

A software routine such as a CSPD routine that provides information to a user comprising the assets to be included in a collection of assets, such as but not limited to a surgical tray being created. Such information may be embodied as a displayed or printed list of the assets.

A software routine such as a CSPD routine that controls the aforementioned at least one apparatus associated with a process step to detect when at least one of asset unit is placed in the surgical tray being created.

A software routine such as a CSPD routine that provides information to a user that such detection has taken place. Such routine may also be utilized to alter the information comprising the assets to be included in a collection, such as removing the asset units that have been detected in a surgical tray from the aforementioned displayed list. Such routine may further provide an indication of asset units detected in a surgical tray, such as but not limited to a displayed list of such detected asset units.

A software routine such as a CSPD routine that provides information to a user that at least one asset unit that does not belong to a collection, or is not a part of usable inventory, has been detected. Such routine may be further configured to direct a user to remove such asset unit from a collection, or to mark such unit for a subsequent treatment such as but not limited to cleansing, decontamination, sterilization, maintenance or obsolescence. Such routine may be further configured to append such asset unit's data record to indicate the mark or the subsequent treatment. Such routine may be further configured to permit a user to override the detection and permit the at least one asset unit to be included in the collection.

A software routine such as a CSPD routine that appends at least one database to relate information detected or measured from a durable means of identifying information of at least one asset unit in a collection to the information detected or measured from a durable means of identifying information of an object for containing such collection, such as but not limited to a surgical tray.

A software routine such as a CSPD routine that shows information about an asset, such as but not limited to information requested by a user about any one or more assets to be included in a collection, and such to provide means to selectively initiate at least one subsequent routine such as but not limited to a routine for marking at least one asset unit for subsequent treatment or for providing assistance in locating at least one asset unit.

A software routine such as a CSPD routine that selectively establishes data coordination between a first apparatus for detecting or measuring at least one healthcare facility asset and at least one additional second apparatus for detecting or measuring at least one healthcare facility asset. In a non-limiting example, a first apparatus may include a scanner such as an interactive scanner 134 configured to measure assets being gathered and included in a collection. A second apparatus may be a dynamic scanner 108. The routine for establishing data coordination may be configured to transmit data to the at least first apparatus and second apparatus, such data including but not limited to the assets in the collection or a subset of the assets in a collection.

A software routine such as a CSPD routine for providing assistance in locating at least one asset unit, such as to be added to a collection, in which information identifying such asset is transmitted to an apparatus for detecting or measuring at least one healthcare facility asset. Such apparatus may include but is not limited to a second scanner such as a dynamic scanner 108, and such apparatus may be subsequently utilized to detect durable means of identifying information of such asset units in usable inventory belonging to the assets being located. Such routine may be further configured to provide for the acquisition and storage of data associated with an asset unit scanned by a dynamic scanner 108 and selected for inclusion in the collection, and may be further configured to coordinate data measures, such as but not limited to identifying information measures, when such at least one asset units scanned by a dynamic scanner 108 and selected for inclusion in a collection are transferred to an object for containing such collection and subsequently scanned by a first scanner. Such coordination of data measure may include but are not limited to a comparison to assure measures match and the provision of a related indicator to a user via a user interface.

A software routine such as a CSPD routine for providing indication to a user that the creation of a collection of assets or asset units is complete. The determination that the collection is complete is preferentially made when at least one apparatus to detect a durable means of identifying information on asset units comprising the collection has detected all asset units present in the collection are matched to the assets designated to be included in the collection. Such routine may also transmit the identifying information on each asset unit present in the collection to a database. Such routine may also relate the asset units' identifying information to the identifying information of the object for containing the collection, such as but not limited to a surgical tray. Such routine may further be configured to provide instructions to a user to prepare such collection for a next process step. Such routine may also be configured to designate the collection for a next process step, and may also acquire and store information related to at least one process step in a database such as but not limited to an HFIL.

The software routines taught for CSPD processes are further conceived to provide functional integration with a product management system of at least one supplier of original equipment that is being managed in the healthcare facility's integrated asset management system, and further configured to provide or derive information related to at least one CSPD process either to or from the product management system. In a non-limiting example, a CSPD process for preparing a collection of assets such as surgical trays for a surgery may include a process step of selecting a surgical tray pre-prepared by the at least one supplier and designating such supplier-prepared surgical tray for a surgery. Accordingly, a software CSPD routine may provide for a user to select at least one supplier-prepared surgical tray, detect or measure a durable information identifier associated with the supplier-prepared surgical tray, verify its contents by utilizing an apparatus such as but not limited to an interactive scanner 134 or a dynamic scanner 108, designate the supplier-prepared surgical tray to a surgery, provide process-related data to at least one database, and provide user instructions for completing a process step or preparing the supplier-prepared surgical tray for a next process. Such routine may also be configured to transmit information related to the use of the supplier-prepared surgical tray, or any other related process in a healthcare facility, back to the product management system of the supplier.

With reference to FIGS. 11*a*-11*f,* a functional module dedicated to operating room (OR) functions may include but is not limited to the following practically applied software steps and routines (i.e. an "OR routine"):

A software routine such as an OR routine that permits an authorized user at a healthcare facility to gain secure access to subsequent software functions.

A software routine such as an OR routine that allows an authorized user to select and gain access to the functional module dedicated to operating room processes.

A software routine such as an OR routine that allows an authorized user to select and differentially gain access to specific operating room processes such as but not limited to processes carried out prior to the beginning of a surgery (pre-surgery), processes carried out during a surgery (live surgery) and processes carried out after completion of a surgery (post-surgery). Such routine may also be configured to provide the user with instructions or specifications related to completing an operating room asset-related process.

A software routine such as an OR routine associated with a pre-surgery process may be configured to guide a user to complete pre-surgery process steps related to healthcare facility assets to be utilized in the surgery, and to provide instructions to assure such process steps are completed in accordance with the process specifications. In a non-limiting example, such routine may be used to guide a user to select a first surgery of at least one surgeries to be carried out, to verify that asset units or collections of assets designated for the first surgery are present, and to verify that all such asset units or collections of assets comprise the asset units designated for the first surgery. Such routine may also be configured to repeat OR routine processes on subsequent surgeries, such as a second surgery, at any time advantageous to the user or to the healthcare facility processes.

A software routine such as an OR routine associated with a pre-surgery process may be further configured to allow a user to select a first surgery of at least one surgeries to be carried out from a list of surgeries derived from information stored in at least one database and provided through a software user interface. Such routine may be further configured to allow a user to review and confirm information existing in at least one database about the surgery.

A software routine such as an OR routine associated with a pre-surgery process may be configured to guide a user through at least one process to verify that asset units designated for the first surgery are present in the operating room. In a non-limiting example, such routine may instruct a user to place at least one asset unit, preferably a collection of assets, in operable proximity to an apparatus for detecting or measuring a durable information identifier, such apparatus including but not limited to an interactive scanner 134 or a dynamic scanner 108. Such routine may be further configured to activate or deactivate the apparatus in accordance with the method or process.

A software routine such as an OR routine associated with a pre-surgery process may be further configured to cause an apparatus, such as an apparatus for detecting or measuring a durable information identifier, to operate to detect the presence of at least one asset unit placed by a user in operable proximity to the apparatus; to operate the apparatus to detect or measure durable information identifiers; and to report detection findings to the user via a user interface.

A software routine such as an OR routine associated with a pre-surgery process may be further configured to provide an indication to a user, such as through a user interface, whenever an at least one asset unit is detected that is discrepant to or not consistent with a healthcare facility process or is not designated for a surgery. In one non-limiting example, an indication to a user may be provided if an apparatus detects an asset unit that is not part of usable inventory, or has been designated for a treatment such as but not limited to cleansing, decontamination, sterilization, maintenance or obsolescence. In another non-limiting example, an indication to a user may be provided if an apparatus detects an asset unit that is not designated for the first surgery as chosen in a previous software process step. In yet another non-limiting example, an indication to a user may be provided if an apparatus fails to detect at least one asset unit that is designated for the first surgery (i.e. a "missing asset"). Further still, such routine may be configured to prevent the completion of further process steps until such discrepancy, inconsistency or missing asset is resolved or allowed by a user override.

A software routine such as an OR routine associated with a pre-surgery process may be further configured to provide a user with any number of means to remedy any discrepancies or inconsistencies detected in relation to an asset unit or to a healthcare facility process. In one non-limiting example, the routine may allow a user to select to repeat the step of using the apparatus for detecting or measuring a durable information identifier. In another non-limiting example, the routine may allow a user to select to use a different apparatus for detecting or measuring a durable information identifier, such as but not limited a handheld apparatus. In yet another non-limiting example, the routine may allow a user to order a missing, discrepant or inconsistent asset unit from a CSPD function. In yet another non-limiting example, the routine may allow a user to accept the missing, discrepant or inconsistent asset unit and allow the process to continue via software override.

A software routine such as an OR routine associated with a pre-surgery process may be further configured to provide a user with an indication via a user interface that pre-surgery process steps for a first surgery have been completed, and may be further configured to guide the user to initiate or complete at least one next process step.

A software routine such as an OR routine associated with a live surgery process may be configured to operate at least one apparatus for detecting or measuring a durable information identifier, such as but not limited to an interactive scanner 134 or a dynamic scanner I 08, to monitor, preferably in a continual manner, the movements of at least one and preferably all asset units present for use during a surgery, and to provide indication of such movements to at least one user via a user interface. Such movements may include but are not limited to transfer of at least one asset unit to or from a surgical tray. Such movements may be detected or measured by a change in detection state of the at least one apparatus.

A software routine such as an OR routine associated with a live surgery process may be further configured to detect any movement of an asset unit that is inconsistent with a healthcare facility process, and to provide an indication of such detection to at least one user via a user interface. In a non-limiting example, at least one apparatus for detecting or measuring a durable information identifier may be placed in proximity to locations of entry points or exit points in an operating room. A process inconsistency during a live surgery process may include the unexpected or unauthorized movement of an asset unit through such entry point or exit point. An OR routine associated with a live surgery process may be configured to provide an indication to at least one user whenever such unexpected or unauthorized movement of an asset may be detected by an apparatus. An OR routine associated with a live surgery process may be further configured to guide a user to remedy such unexpected or unauthorized movement of an asset.

A software routine such as an OR routine associated with a live surgery process may be further configured to show information about an asset, such as but not limited to information requested by a user about any one or more assets to be included in a collection. Such routine may also be configured to provide means to selectively initiate at least one subsequent routine such as but not limited to a routine for marking at least one asset unit for subsequent treatment or for providing assistance in locating at least one asset unit. Such routine may also be configured to designate at least one asset unit for an alternate process step. In a non-limiting example, should a surgical instrument be exposed to an unexpected contaminant during a surgery, such routine may be utilized to designate such instrument for a cleansing, decontamination or sterilization process, may further be utilized to track the instrument through such alternate process, and may further be configured to update at least one database with process-related information. Such routine may also be configured to transmit information to or from a CSPD function relating to an asset unit. A non-limiting example of such information may be an order to provide an asset unit from a CSPD function to a live surgery.

A software routine such as an OR routine associated with a live surgery process may be further configured to allow a user to designate a live surgery as complete. Such routine may also provide indication to at least one additional user that the live surgery is complete. Such routine may also provide indication and related designation to a software application in a healthcare facility that the live surgery is complete, and accordingly may initiate next process steps.

A software routine such as an OR routine associated with a post-surgery process may be configured to support, manage or instruct any number of post-surgery processes. Of primary benefit to the methods, such software routine may be configured to verify that all asset units that were designated for a surgery are accounted for after completion of the surgery.

More specifically, a software routine such as an OR routine associated with a post-surgery process may be configured to permit a user, via a user interface, to select at least one asset unit or collection of assets from all such asset units or collections designated for a completed surgery. Such routine may be further configured to direct a user to place such selected at least one asset unit or collection of assets in operable proximity to an apparatus for detecting or measuring a durable information identifier, such apparatus including but not limited to an interactive scanner 134 or a dynamic scanner 108. Such routine may be further configured to activate or deactivate the apparatus in accordance with the method or process.

A software routine such as an OR routine associated with a post-surgery process may be further configured to cause an apparatus, such as an apparatus for detecting or measuring a durable information identifier, to operate to detect the presence of at least one asset unit placed by a user in operable proximity to the apparatus; to operate the apparatus to detect or measure durable information identifiers; and to report detection findings to the user via a user interface.

A software routine such as an OR routine associated with a post-surgery process may be further configured to make a comparison of detected durable information identifiers, including but not limited to durable information identifiers of asset units comprising a collection of assets, with the durable information identifiers of asset units determined in a pre-surgery process and designated for the surgery. Such comparison may include but is not limited to a count of such asset units.

A software routine such as an OR routine associated with a post-surgery process may be further configured to provide an indication to a user, such as through a user interface, whenever a detection or comparison of durable information identifiers of asset units in a post-surgery process is discrepant to or not consistent with the durable information identifiers of asset units determined in a pre-surgery process and designated for the surgery. In one non-limiting example, an indication to a user may be provided if an apparatus detects an asset unit is located in an object for containing a collection, such as but not limited to a surgical tray, inconsistent with the object to which the asset was designated in a pre-surgery process step. In other words, an indication to a user might provide information that an asset unit is in a wrong object for containing the collection. In another non-limiting example, an indication to a user may be provided if an apparatus fails to detect at least one asset unit that is expected to be located in an object for containing a collection (i.e. a "missing asset", such as but not limited to a surgical tray. Further still, such routine may be configured to prevent the completion of further process steps until such discrepancy, inconsistency or missing asset is resolved or allowed by a user override.

A software routine such as an OR routine associated with a post-surgery process may be further configured to provide a user with any number of means to remedy any discrepancies or inconsistencies detected in relation to an asset unit or to a healthcare facility process. In one non-limiting example, the routine may allow a user to select to repeat the step of using the apparatus for detecting or measuring a durable information identifier. In another non-limiting example, the routine may allow a user to select to use a different apparatus for detecting or measuring a durable information identifier, such as but not limited a handheld apparatus. In a particular use of such means to remedy, an apparatus such as a handheld apparatus may be used to detect whether a missing asset has been left inside the subject undergoing the surgery. In yet another non-limiting example, the routine may allow a user to accept the missing, discrepant or inconsistent asset unit and allow the process to continue via software override.

A software routine such as an OR routine associated with a post-surgery process may be further configured to provide a user with the ability to do manual count of asset units in a collection, and verify in the software routine that the manual count either does or does not match a count of the asset units as determined by an apparatus. Such routine may be further configured to guide a user to remedy any discrepancy in count, such as by means of remedies taught herein.

A software routine such as an OR routine associated with a post-surgery process may be further configured to transmit information relating to at least one discrepant asset unit to a dynamic scanner 108. Such dynamic scanner 108 may then be used in modes of operation as taught herein to selectively detect or measure a durable means of identification only associated with the at least one discrepant asset unit. Such routine may be configured to further receive information from a dynamic scanner 108 relating to at least one discrepant asset unit. Such information received from a dynamic scanner 108 may include but is not limited to an indicator that at least one discrepancy is resolved.

A software routine such as an OR routine associated with a post-surgery process may be further configured to perform routines such as but not limited to detecting, measuring, counting, comparing, identifying a discrepancy or resolving a discrepancy related to assets or asset units associated with at least one supplier of original equipment that is being managed in the healthcare facility's integrated asset management system. In a non-limiting example, the asset units of a supplier-prepared surgical tray designated for the surgery in a pre-surgery process may be detected and counted by an apparatus for detecting or measuring a durable means of identification. Such software routine may be utilized to initiate the detection process, make comparisons or counts of asset units and provide means to resolve any discrepancies detected between expected results and determined results. Such software routine may be further configured to verify supplier asset units that were consumed in the surgery. A non-limiting example of such consumed assets may include an implantable device. Such software routine may be further configured to transmit information arising from post-surgery processes to the product management system of the supplier.

A software routine such as an OR routine associated with a post-surgery process may be further configured to provide a user with an indication via a user interface that post surgery process steps for a first surgery have been completed, and may be further configured to guide the user to initiate or complete at least one next process step.

These and other software routines are readily implemented and practically applied to implement the invented methods and apparatuses as taught herein. No software routine recited herein is meant to suggest a limitation to any other software routine that may be conceived to implement the methods.

The invention is not limited in any way to the embodiments disclosed herein. In this regard, no attempt is made to show structural details of the disclosed apparatuses or process details of the disclosed methods in more detail than is necessary for a fundamental understanding of the disclosed apparatuses, methods and systems. The description is intended only to make apparent to those skilled in the art how the several forms of the invention may be embodied in practice.

What is claimed is:

1. A healthcare facility process management method wherein data from an asset management system provides information used to manage a healthcare facility process, the method comprising the steps of:
    operating an asset management system comprising a plurality of physical asset units, each physical asset unit carrying a durable information identifier;
    utilizing one or more durable information identifier detectors to obtain data relating to physical asset unit use at points of healthcare facility processes performed on the physical asset units;
    processing the data relating to physical asset unit use at points of healthcare facility processes to obtain additional data related to the carrying out of the healthcare facility processes;
    retrieving process data relating to the healthcare facility processes from the asset management system by using a computational processor of a computer system having the computational processor and memory; and
    analyzing the process data with the data relating to physical asset unit use from the one or more durable information identifier detectors with the computational processor, wherein the analyzed process data with the data relating to physical asset unit use from the one or more durable information identifier detectors provide characteristics of the managed healthcare facility processes.

2. The method of claim 1 in which the data comprises data arising from a plurality of physical asset units tracked in the asset management system, and the retrieving step further comprises retrieving process data that are independent of the asset management system.

3. The method of claim 1 in which the method is implemented in a multiplicity of facilities and any combination of data from the multiplicity of facilities is utilized in the method.

4. The method of claim 3 wherein each facility of the multiplicity of facilities uses the asset management system.

5. The method of claim 1 further comprising the use of patient experiences data, patient symptoms data, or outcome metrics data arising from patient monitoring occurring before, during or after an interaction with a healthcare facility.

6. The method of claim 5 in which the use of patient experiences and outcome metrics further comprises identifying relationships between healthcare facility processes and patient outcomes.

7. The method of claim 1 further comprising integration of the process data and/or the analyzed process data with a supply chain management system.

8. The method of claim 7 wherein the process data and/or the analyzed process data is used for purchasing, inventory control, maintenance of one or more physical asset units of the plurality of physical asset units, and/or disposition of one or more physical asset units of the plurality of physical asset units.

9. The method of claim 1 further comprising integration of the process data and/or the analyzed process data, with a process optimization system or a quality management system.

10. The method of claim 1 in which the method further comprises the use of software to carry out one or more of the following steps:

analyzing process adjustments arising from data or analyses associated with process metrics;

comparing pre-adjustment metrics for the purposes of quantifying or qualifying process improvement or the lack thereof;

determining correlations between data related to a first managed process and data related to second managed processes, to determine process influences between the first managed process and the second managed processes;

determining correlations between process data associated with a healthcare facility and the process data of other facilities;

determining correlations between process data associated with a first human operator and second human operators in a healthcare facility; and determining measures of healthcare facility process characteristics in relationship to one or more socioeconomic measures or statistics associated with the population of persons for which the facility serves.

11. The method of claim 1 wherein the durable information identifier is an RFID-based technology.

12. A healthcare facility process management method wherein data from an asset management system provides information used to manage a healthcare facility process, the method comprising the steps of:

operating an asset management system comprising a plurality of asset units, each asset unit carrying a durable information identifier;

utilizing one or more durable information identifier detectors to obtain data relating to asset unit use at points of healthcare facility processes performed on the asset units;

processing the data relating to asset unit use at points of healthcare facility processes to obtain additional data related to the carrying out of the healthcare facility processes, wherein information received by the one or more durable information identifier detectors relates to tracking process uses of the asset units and the information is appended to one or more databases containing information about the asset units as utilized by a facility for asset and process management;

retrieving process data relating to the healthcare facility processes from the asset management system by using a computational processor, wherein data acquisition devices configured to acquire such additional data are utilized in relation to the facility operational processes, and wherein information received by the devices is appended to the one or more databases containing information about each process use; and operationally coupling the data acquisition devices and the one or more durable information identifier detectors to a data acquisition system, wherein coupling is achieved by interfacing the data acquisition devices and the one or more durable information identifier detectors to an information technology platform utilizing a computer-based data acquisition system linked to the one or more databases, wherein the data acquisition devices and the one or more durable information identifier detectors further comprise computer-based systems including computers, processors, memory, displays or peripheral devices, and wherein the computer-based systems utilize software practically applied to control the data acquisition devices and the one or more durable information identifier detectors.

* * * * *